(12) United States Patent
Caddick et al.

(10) Patent No.: US 6,605,754 B1
(45) Date of Patent: Aug. 12, 2003

(54) DNA CONSTRUCTS AND PLANTS INCORPORATING THEM

(75) Inventors: Mark X. Caddick, Liverpool (GB); Andrew J. Greenland, Maidenhead (GB); Kay V. Riddell, West Lothian (GB); Wolfgang W. Schuch, Berkshire (GB); Arthur B. Tomsett, Merseyside (GB)

(73) Assignee: Syngenta Limited, Berkshire (GB)

( * ) Notice: Subject to any disclaimer, the term of this patent is extended or adjusted under 35 U.S.C. 154(b) by 0 days.

(21) Appl. No.: 09/045,881

(22) Filed: Mar. 17, 1998

Related U.S. Application Data

(63) Continuation-in-part of application No. 08/374,783, filed as application No. PCT/GB93/01605 on Jul. 29, 1993, now abandoned.

(30) Foreign Application Priority Data

Apr. 13, 1992 (GB) .............................................. 9208117
Apr. 24, 1992 (GB) .............................................. 9208954

(51) Int. Cl.⁷ ............................ A01H 5/00; A01H 5/10; C12N 5/04; C12N 15/31; C12N 15/82
(52) U.S. Cl. ...................... 800/278; 800/288; 800/298; 800/317; 800/317.3; 800/320; 800/320.1; 435/412; 435/414; 435/419; 435/430; 435/468
(58) Field of Search .......................... 536/24.1, 23.74; 800/278, 288, 317.3, 320.1, 317, 298, 320; 435/412, 419, 414, 430, 468

(56) References Cited

U.S. PATENT DOCUMENTS 5,723,764 A    3/1998  Oliver ........................ 800/205

FOREIGN PATENT DOCUMENTS

| EP | 0 459 643 | | 12/1991 |
| GB | 9208117.3 | * | 4/1992 |
| WO | WO 90/08826 | | 8/1990 |
| WO | WO 93/0237 | | 3/1993 |
| WO | WO 93/21334 | | 10/1993 |
| WO | WO 94/03619 | | 2/1994 |

OTHER PUBLICATIONS

Napoli et al. The Plant Cell. 1989. vol. 2: 278–289.*
Ohshima et al. The Plant Cell. 1990. Feb. issue. vol. 2: 95–106.*
Linthorst et al. The Plant Cell. 1989. Mar. issue. vol. 1: 285–291.*
Gwynne et al. Gene. 1987. vol. 51: 205–216.*
Felenbok et al. Gene. 1988. Dec. issue. vol. 73: 385–396.*
Roberts et al., Dependence of Ethanolic Fermentation, Cytoplasmic pH Regulation, and Viability on the Activity . . . , 1989, Plant Physiol, vol. 89, pp. 1275–1278.*
Ellis et al., Maize Adh–1 promoter sequences control anaerobic regulation: addition upstream promoter elements . . . , 1987, The EMBO Journal, vol. 6, No. 1, pp. 11–16.*
Goring et al., Transformation of a partial nopaline synthase gene into tobacco suppresses the expression of resident wild–type gene, Mar. 1991, Botant, vol. 88, pp. 1770–1774.*
Felenbok et al., The ethanol utilization regulon of Asgergillus: the alc A–alc R system as a tool for the expression of recombinant proteins, 1991, Journal of Biotechnology, vol. 17, pp. 11–18.*
Benfey et al., The Cauliflower Mosaic Virus 35S Promoter: Combinatiorial Regulation of Transcription in Plants, Nov. 1990, Science, pp. 959–966.*
Schena et al., A steroid–inducible gene expression system for plant cells, Dec. 1991, Genetics, vol. 88, pp. 10421–10425.*
Boetti et al., Efficiency of Physical (Light) or Chemical (ABA, Tetracycline, CuSO4 or 2–CBSU)–Stimulus–Dependent gus . . . , Jul. 5, 1999, Biotechnology and Bioengineering, vol. 64, No. 1, pp. 1–13.*
Caddick et al., An ethanol unducible gene switch for plants used to manipulate carbon metabolism, Nature Biotechnology, Feb. 1998, vol. 16, pp. 177–180.
Slater et al, Characterisation of the ethanol–inducible alc gene expression system for transgenic plants, The Plant Journal, 1998, vol. 16, pp. 127–132.
Schena et al., A steroid–inducible gene expression system for plant cells, Proc. Natl. Acad. Sci. USA, Dec. 1991, vol. 88, pp. 104211–10425.
Van de Rhee et al., Analysis of regulatory elements Involved in the Induction of two tobaco genes by salicylate treatment and virus infection, The Plant Cell, Apr. 1990, vol. 2, pp. 357–366.
Olive et al., Functional properties of the anaerobic responsive element of the maize Adh 1 gene, Plant Molecular Biology, 1990, vol. 15, pp. 593–604.
Ma et al., Yeast activators stimulate plant gene expression, Nature, Aug. 18, 1988, vol. 334, pp. 631–633.

(List continued on next page.)

*Primary Examiner*—David T. Fox
*Assistant Examiner*—Russell Kallis
(74) *Attorney, Agent, or Firm*—Morgan, Lewis & Bockius LLP

(57) ABSTRACT

The invention relates to a chemically-inducible plant gene expression cassette and to plant cells transformed therewith. The expression cassette is suitable for use in any dicotyledonous or monocotyledonous plant. It comprises a first promoter operatively linked to a regulator sequence which encodes a regulator protein, and an inducible promoter operatively linked to a target gene, the inducible promoter being activated by the regulator protein in the presence of an effective exogenous inducer whereby application of the inducer causes expression of the target gene. The regulator sequence may be derived from the alcR gene, and the inducible promoter may be derived from the alcA gene promoter (both obtainable from *Aspergillus nidulans*). A chimeric promoter comprising an upstream regulatory region and a heterologous downstream transcription initiation region is also disclosed. The regulatory sequence may be derived from the alcA gene promoter.

17 Claims, 11 Drawing Sheets

OTHER PUBLICATIONS

Vilardell et al., Regulation of the maize rab17 gene promoter in transgenic heterologous systems, Plant Molecular Biology, 1991, vol. 17, pp. 985–993.

Gatz et al., Regulation of a modified CaMV 35S promoter by the Tn10–encoded Tet repressor in transgenic tobacco, Mol Gen Genet, 1991, vol. 227, pp. 229–237.

* cited by examiner

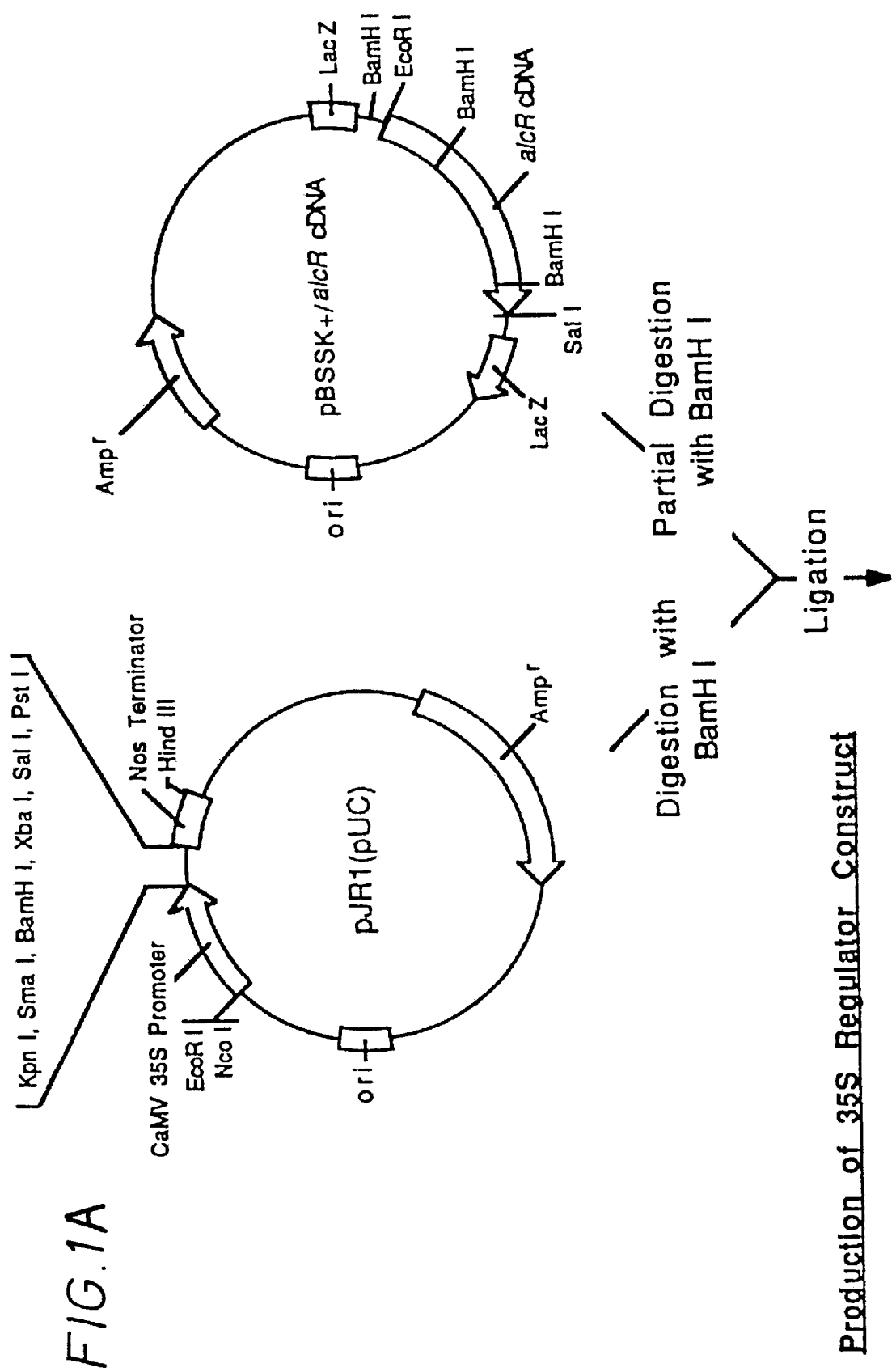

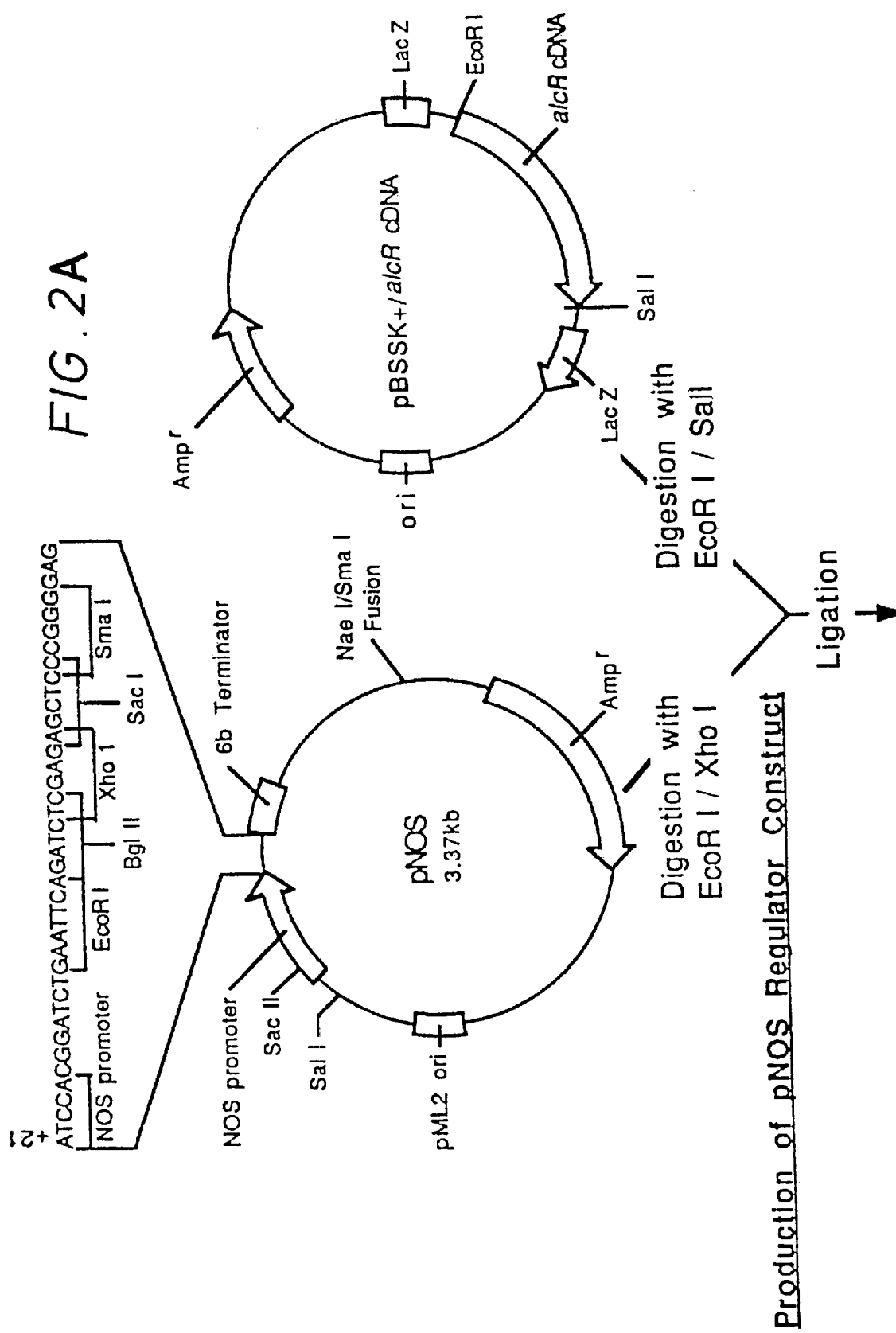

Production of Reporter Construct

DNA CONSTRUCTS AND PLANTS INCORPORATING THEM

This is a continuation-in-part of U.S. application Ser. No. 08/374,783 filed Sep. 6, 1995, now abandoned, which is a national stage application under 35 U.S.C. 371 of Intl. Appln. No. PCT/GB93/01605 designating the U.S. and filed Jul. 29, 1993, now abandoned.

BACKGROUND OF THE INVENTION

1. Field of the Invention

The present invention relates to DNA constructs and plants incorporating them. In particular, it relates to expression cassettes and promoter sequences for the expression of genes in plants.

2. Description of Related Art

Gene expression is controlled by regions upstream (5') of the protein encoding region, commonly referred to as the "promoter". A promoter may be constitutive, tissue-specific, developmentally-programmed or inducible.

Manipulation of crop plants to improve characteristics (such as productivity or quality) requires the expression of foreign or endogenous genes in plant tissues. Such genetic manipulation therefore relies on the availability of means to control gene expression as required; for example, on the availability and use of suitable promoters which are effective in plants. It is advantageous to have the choice of a variety of different promoters so that the most suitable promoter may be selected for a particular gene, construct, cell, tissue, plant or environment. A range of promoters are known to be operative in plants.

Within the promoter region there are several domains which are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence which defines the transcription start point for the structural gene. The precise length of the core promoter region is indefinite but it is usually well-recognisable. Such a region is normally present, with some variation, in all promoters. The base sequences lying between the various well-characterised "boxes" appear not to be of great importance.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions.

SUMMARY OF THE INVENTION

Several naturally-occurring promoters and associated gene expression systems are known. The best characterised regulatory systems are those of bacteria in which the specific interactions between DNA-binding proteins (repressors) and the target DNA sequences (operators) results in the negative repression of gene activity.

The alcA/alcR gene activation system from the fungus *Aspergillus nidulans* is also well characterised. The ethanol utilization pathway in *A nidulans* is responsible for the degradation of alcohols and aldehydes. Three genes have been shown to be involved in the ethanol utilization pathway. Genes alcA and alcR have been shown to lie close together on linkage group VII and aldA maps to linkage group VIII (Pateman J H et al, 1984, Proc. Soc. Lond, B217:243–264; Sealy-Lewis H M and Lockington R A, 1984, Curr. Genet, 8:253–259). Gene alcA encodes ADHI in *A nidulans* and aldA encodes AldDH, the second enzyme responsible for ethanol utilization. The expression of both alcA and aldA are induced by ethanol and a number of other inducers (Creaser E H et al, 1984, Biochemical J, 255:449–454) via the transcription activator alcR. The alcR gene and a co-inducer are responsible for the expression of alcA and aldA since a number of mutations and deletions in alcR result in the pleiotropic loss of ADHI and aldDH (Felenbok B et al, 1988, Gene, 73:385–396; Pateman et al, 1984; Sealy-Lewis & Lockington, 1984). The ALCR protein activates expression from alcA by binding to three specific sites in the alcA promoter (Kulmberg P et al, 1992, J. Biol. Chem, 267:21146–21153).

The alcR gene was cloned (Lockington R A et al, 1985, Gene, 33:137–149) and sequenced (Felenbok et al, 1988). The expression of the alcR gene is inducible, autoregulated and subject to glucose repression mediated by the CREA repressor (Bailey C and Arst H N, 1975, Eur. J. Biochem, 51:573–577; Lockington R A et al, 1987, Mol. Microbiology, 1:275–281; Dowzer C E A and Kelly J M, 1989, Curr. Genet, 15:457–459; Dowzer C E A and Kelly J M, 1991, Mol. Cell. Biol, 11:5701–5709). The ALCR regulatory protein contains 6 cysteines near its N terminus coordinated in a zinc binuclear cluster (Kulmberg P et al, 1991, FEBS Letts, 280:11–16). This cluster is related to highly conserved DNA binding domains found in transcription factors of other ascomycetes. Transcription factors GAL4 and LAC9 have been shown to have binuclear complexes which have a cloverleaf type structure containing two Zn(II) atoms (Pan T and Coleman J E, 1990, Biochemistry, 29:3023–3029; Halvorsen Y D C et al, 1990, J. Biol. Chem, 265:13283–13289). The structure of ALCR is similar to this type except for the presence of an asymmetrical loop of 16 residues between Cys-3 and Cys-4. ALCR positively activates expression of itself by binding to two specific sites in its promoter region (Kulmberg P et al, 1992, Molec. Cell. Biol, 12:1932–1939).

The regulation of the three genes, alcR, alcA and aldA, involved in the ethanol utilization pathway is at the level of transcription (Lockington et al, 1987; Gwynne D et al, 1987, Gene, 51:205–216; Pickett et al, 1987, Gene, 51:217–226).

There are two other alcohol dehydrogenases present in *A nidulans*. ADHII is present in mycelia grown in non-induced media and is repressible by the presence of ethanol. ADHII is encoded by alcB and is also under the control of alcR (Sealy-Lewis & Lockington, 1984). A third alcohol dehydrogenase has also been cloned by complementation with a adh-strain of *S cerevisiae*. This gene alcC, maps to linkage group VII but is unlinked to alcA and alcR. The gene, alcC, encodes ADHIII and utilizes ethanol extremely weakly (McKnight G L et al, 1985, EMBO J, 4:2094–2099). ADHIII has been shown to be involved in the survival of *A nidulans* during periods of anaerobic stress. The expression of alcC is not repressed by the presence of glucose, suggesting that it may not be under the control of alcR (Roland L J and Stromer J N, 1986, Mol. Cell. Biol, 6:3368–3372).

In summary, *A nidulans* expresses the enzyme alcohol dehydrogenase I (ADH1) encoded by the gene alcA only when it is grown in the presence of various alcohols and ketones. The induction is relayed through a regulator protein encoded by the alcR gene and constitutively expressed. In the presence of inducer (alcohol or ketone), the regulator protein activates the expression of the alcA gene. The regulator protein also stimulates expression of itself in the presence of inducer. This means that high levels of the ADH1enzyme are produced under inducing conditions (ie when alcohol or ketone are present). Conversely, the alcA gene and its product, ADH1, are not expressed in the absence of inducer. Expression of alcA and production of the enzyme is also repressed in the presence of glucose.

Thus the alcA gene promoter is an inducible promoter, activated by the alcR regulator protein in the presence of inducer (ie by the protein/alcohol or protein/ketone combination). The alcR and alcA genes (including the respective promoters) have been cloned and sequenced (Lockington R A et al, 1985, Gene, 33:137–149; Felenbok B et al, 1988, Gene, 73:385–396; Gwynne et al, 1987, Gene, 51:205–216).

Alcohol dehydrogenase (adh) genes have been investigated in certain plant species. In maize and other cereals they are switched on by anaerobic conditions. The promoter region of adh genes from maize contains a 300 bp regulatory element necessary for expression under anaerobic conditions. However, no equivalent to the alcR regulator protein has been found in any plant. Hence the alcR/alcA type of gene regulator system is not known in plants. Constitutive expression of alcR in plant cells does not result in the activation of endogenous adh activity.

The knowledge of mechanisms by which gene expression is regulated in eukaryotes is much less detailed than the knowledge of bacterial systems. In yeast and mammalian cells a large number of binding sites for putative regulatory proteins have been identified in promoter sequences, and in some cases the proteins responsible have also been isolated. However, only in a few instances are the molecular details known of the protein-DNA interactions and the mechanism by which transcription is regulated. In plants, regulation of gene expression is understood at only a rudimentary level. Several regulatory elements have been identified in promoter sequences, and some regulatory proteins examined at a preliminary level. Many such proteins have yet to be isolated and the details of the mechanisms involved have yet to be elucidated.

The control of expression of heterologous genes in plant tissues is important for successful genetic manipulation of plants to alter and/or improve phenotypic characteristics. Promoters and/or regulatory components from bacteria, viruses, fungi and plants have been used to control gene expression in plant cells. For example, two well-characterised bacterial operator-repressor systems have been used to show negative (down) regulation of gene expression in plant cells. A modified bacterial tet operator-repressor system has been shown to repress gene expression in electroporated plant cells. Gene expression from the CAT gene was reduced by the placing of tet operators in the 35S promoter (Gatz and Quail, 1988, Proc. Natl. Acad. Sci. USA, 85:1394–1397). Functional tet repressor expressed from an integrated gene also represses expression from an integrated β-glucuronidase gene (gus) driven by the 35S promoter containing two inserted tet operators (Gatz et al, 1991, Mol. Gen. Genet, 227:229–237).

The lac operator-repressor system has been used to repress gene expression in tobacco cells. Functional LacI protein expressed from a stably integrated lacI gene repressed expression from a stably integrated gus gene controlled by the maize chlorophyll a/b binding protein (CAB) promoter containing a lac operator. Derepression of gus activity occurred when the cells were incubated with the inducer iso-propyl thiogalactoside (IPTG) showing that repression of gene activity is specifically due to the lacI gene product (Wilde R J et al, 1992, EMBO J, 11:1251–1259).

As stated above, successful genetic manipulation relies on the availability of means to control gene expression as required. The scientist may use a suitable expression cassette (incorporating one or more promoters and other components) to regulate gene expression in the desired manner. The ability to enhance or reduce gene expression to achieve a desired phenotypic effect according to external circumstances is particularly advantageous. We now provide a novel plant gene expression cassette which allows external activation of target gene expression within plants.

DETAILED DESCRIPTION OF SPECIFIC EMBODIMENTS

According to a first aspect of the invention, there is provided a chemically-inducible plant gene expression cassette comprising a first promoter operatively linked to a regulator sequence which encodes a regulator protein, and an inducible promoter operatively linked to a target gene, the inducible promoter being activated by the regulator protein in the presence of an effective exogenous inducer whereby application of the inducer causes expression of the target gene.

The first promoter may be constitutive, or tissue-specific, developmentally-programmed or even inducible. The regulator-sequence is preferably the alcR gene obtainable from *Aspergillus nidulans*, encoding the alcR regulator protein.

The inducible promoter is preferably the alcA gene promoter obtainable from *Aspergillus nidulans*, or a "chimeric" promoter derived from the regulatory sequences of the alcA promoter and the core promoter region from a gene promoter which operates in plant cells (including any plant gene promoter). The alcA promoter or a related "chimeric" promoter is activated by the alcR regulator protein when an alcohol or ketone inducer is applied.

The inducible promoter may also be derived from the aldA gene promoter, the alcB gene promoter or the alcC gene promoter obtainable from *Aspergillus nidulans*.

The target gene may be an endogenous plant gene or a foreign gene, and may be a single gene or a series of genes. The target gene sequence encodes at least part of a functional protein or an antisense sequence.

The inducer may be any effective chemical (such as an alcohol or ketone). Suitable chemicals for use with an alcA/alcR-derived cassette include those listed by Creaser et al (1984, Biochem J, 225, 449–454) such as butan-2-one (ethyl methyl ketone), cylcohexanone, acetone, butan-2-ol, 3-oxobutyric acid, propan-2-ol, ethanol.

The gene expression cassette is responsive to an applied exogenous chemical inducer enabling external activation of expression of the target gene regulated by the cassette. The expression cassette is highly regulated and suitable for general use in plants.

The two parts of the expression cassette may be on the same construct or on separate constructs. The first part comprises the regulator cDNA or gene sequence subcloned into an expression vector with a plant-operative promoter driving its expression. The second part comprises at least part of an inducible promoter which controls expression of a downstream target gene. In the presence of a suitable inducer, the regulator protein produced by the first part of the cassette will activate the expression of the target gene by stimulating the inducible promoter in the second part of the cassette.

As an example of the invention, a gene expression cassette was constructed comprising the *Aspergillus nidulans* alcR gene under control of a constitutive promoter and an alcA:35S inducible "chimeric" promoter linked to the chloramphenicol acetyl transferase (CAT) gene from *E coli*. Constructs representing the two parts of this expression cassette were tested in *Aspergillus nidulans*. For example:

(1) An alcR cDNA was expressed in *A nidulans* by placing it downstream from the CaMV 35S or nos promoter. Transformants of an alcR⁻strain were shown to be wild type (alcR⁺) with respect to growth on ethanol as sole carbon source, showing that the alcR construct was expressing the regulator protein.

(2) A construct containing a CAT gene downstream from the alcA:35S "chimeric" promoter was tested in a (alcR⁺) *A nidulans* strain. The CAT gene was used as the target gene because it is a suitable reporter gene for monitoring gene expression. CAT activity was alcohol-inducible (ie repressor protein plus inducer were activating the "chimeric" promoter), showing that the "chimeric" promoter is functional.

(3) The regulator alcR construct and the alcA reporter construct were co-transformed into an alcR⁻A⁻deletion strain. Any expression of the CAT reporter gene is induced by the alcR regulator protein produced by the regulator construct, without interference from a wild-type regulator protein. The alcA:35S chimeric promoter is inducible: the promoter drives expression of the CAT reporter gene when the regulator protein and inducer are present. Thus the gene expression cassette (comprising the alcR and alcA constructs) is functional and chemically-inducible (ie subject to external activation).

This invention is based on the construction of the above type of expression cassette and on our recognition that the functional elements of the cassette are suitable for application in other organisms, particularly in plants (such as tobacco, tomato, canola, sugarbeet, sunflower, maize, or wheat).

In practice the construct or constructs comprising the expression cassette of the invention will be inserted into a plant by transformation. Expression of target genes in the construct, being under control of the chemically switchable promoter of the invention, may then be activated by the application of a chemical inducer to the plant.

Any transformation method suitable for the target plant or plant cells may be employed, including infection by *Agrobacterium tumefaciens* containing recombinant Ti plasmids, electroporation, microinjection of cells and protoplasts, microprojectile transformation and pollen tube transformation. The transformed cells may then in suitable cases be regenerated into whole plants in which the new nuclear material is stably incorporated into the genome. Both transformed monocot and dicot plants may be obtained in this way.

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

The invention further provides a plant cell containing a gene expression cassette according to the invention. The gene expression cassette may be stably incorporated in the plant's genome by transformation. The invention also provides a plant tissue or a plant comprising such cells, and plants or seeds derived therefrom.

The invention further provides a method for controlling plant gene expression comprising transforming a plant cell with a chemically-inducible plant gene expression cassette which has a first promoter operatively linked to a regulator sequence which encodes a regulator protein, and an inducible promoter operatively linked to a target gene, the inducible promoter being activated by the regulator protein in the presence of an effective exogenous inducer whereby application of the inducer causes expression of the target gene.

As an example of the invention, we have demonstrated the functioning of alcR/alcA constructs in plant cells, and have shown that the system is useful as an inducible plant gene expression cassette. Regulator and reporter constructs were transformed separately and together into maize plant protoplasts for transient gene expression assays. Expression of the CAT gene from the alcA promoter in maize protoplasts incubated in the presence of ethanol (inducer) is dependent on the presence of the alcR gene (expressing the regulator protein). Stably transformed tobacco plants containing the alcR/alcA-CAT expression cassette were also produced. High levels of reporter (CAT) gene expression were only obtained in the presence of the alcR regulator gene product and following chemical induction by cyclohexanone. High levels of activity from the alcA-CAT reporter gene construct were not obtained under a range of growth conditions such as anaerobis, indicating that reporter gene expression was not induced by conditions that might normally be expected to induce plant alcohol dehydrogenases.

The inducible promoter forming part of the gene expression cassette according to the invention may be a "chimeric" promoter sequence, created as described above by fusing heterologous upstream and downstream regions. Such a chimeric promoter may have independent utility as an alternative plant promoter for use in genetic manipulation. Comai et al have previously described a chimeric plant promoter combining elements of the CaMV35S and the mannopine synthase (mas) promoters (1990, Plant Mol Biol, 15:373–381). In electroporated tobacco cells, the yeast GAL4 protein has been shown to stimulate CAT gene expression controlled from a 35S promoter which had GAL4 binding sites upstream from the TATA box (Ma J et al, 1988, Nature, 334:631–633).

According to a second aspect of the invention, there is provided a chimeric promoter comprising an upstream region containing a promoter regulatory sequence and a downstream region containing a transcription initiation sequence, characterised in that said upstream and downstream regions are heterologous.

The upstream region may contain a constitutive, a tissue-specific, a developmentally-programmed or an inducible promoter regulatory sequence. There may be one or more regulatory sequences in the upstream region. The downstream region is a core promoter region. The upstream and downstream regions correspond to sequences isolated respectively from different sources. The upstream or downstream regions are fused together. The upstream and/or downstream regions may be synthesised.

The upstream sequence is preferably derived from the inducible alcA gene promoter obtainable from *Aspergillus* nidulans. The upstream sequence may also be derived from the aldA, alcB or alcC gene promoters obtainable from *Aspergillus nidulans*. The downstream sequence may be derived from the core promoter region of any plant-operative promoter (such as the CaMV35S promoter, MFS14, MFS18, GSTII-27, pMR7, Polygalacturonase promoters), or may be synthesised from consensus sequences.

The chimeric promoter may be operatively linked to one or more target gene sequences encoding at least part of a functional protein or an antisense RNA. The target gene may be any endogenous plant gene or any foreign gene.

In practice the promoter of the invention will be inserted as a promoter sequence in a recombinant gene construct destined for use in a plant. The construct will then be inserted into the plant by transformation. Any plant species may be transformed with the construct, and any suitable transformation method may be employed.

The invention further provides a plant cell containing a chimeric promoter according to the invention. The chimeric promoter may be stably incorporated in the plant's genome by transformation. The invention also provides a plant tissue or a plant comprising such cells, and plants or seeds derived therefrom.

As an example of the invention, a chimeric gene promoter sequence has been produced by fusing a regulatory region from the *Aspergillus nidulans* alcA gene promoter to part of the −70 core region of the Cauliflower mosaic virus (CaMV) 35S promoter (see Example 2 and FIG. 3). The alcA:35S chimeric promoter sequence was linked to the chloramphenicol acetyl transferase (CAT) gene from *E coli* and transformed into an (alcR$^+$)*A nidulans* strain. The CAT gene was used as a reporter gene to monitor gene expression. CAT production indicated that the chimeric promoter was functioning correctly (see Example 3).

The alcA:35S chimeric promoter is also suitable for use in any plant. Transient expression assays in maize protoplasts (Example 4) and expression from stably-incorporated genes in tobacco (Example 5) have shown that the alcA:35S promoter is fully functional in plant cells.

BRIEF DESCRIPTION OF THE DRAWINGS

The invention will now be described by way of example only with reference to the accompanying drawings in which:

FIGS. 1A–1B show a scheme for the production of the 35S regulator construct.

FIGS. 2A–2B show a scheme for the production of the pNOS regulator construct.

EXAMPLE 1

Production of the alcR Regulator Construct

The alcR genomic DNA sequence has been published, enabling isolation of a sample of alcR cDNA.

The alcR cDNA was cloned into two different expression vectors, pJR1 (pUC) and pNOS. pJR1 contains the Cauliflower Mosaic Virus 35S promoter and pNOS contains the nos gene promoter from the Ti Plasmid of *Agrobacterium tumefaciens*. Both of these promoters are constitutive plant promoters and will continually express the regulator protein. The nos polyadenylation signal is used in both the expression vectors.

Figure 1B:
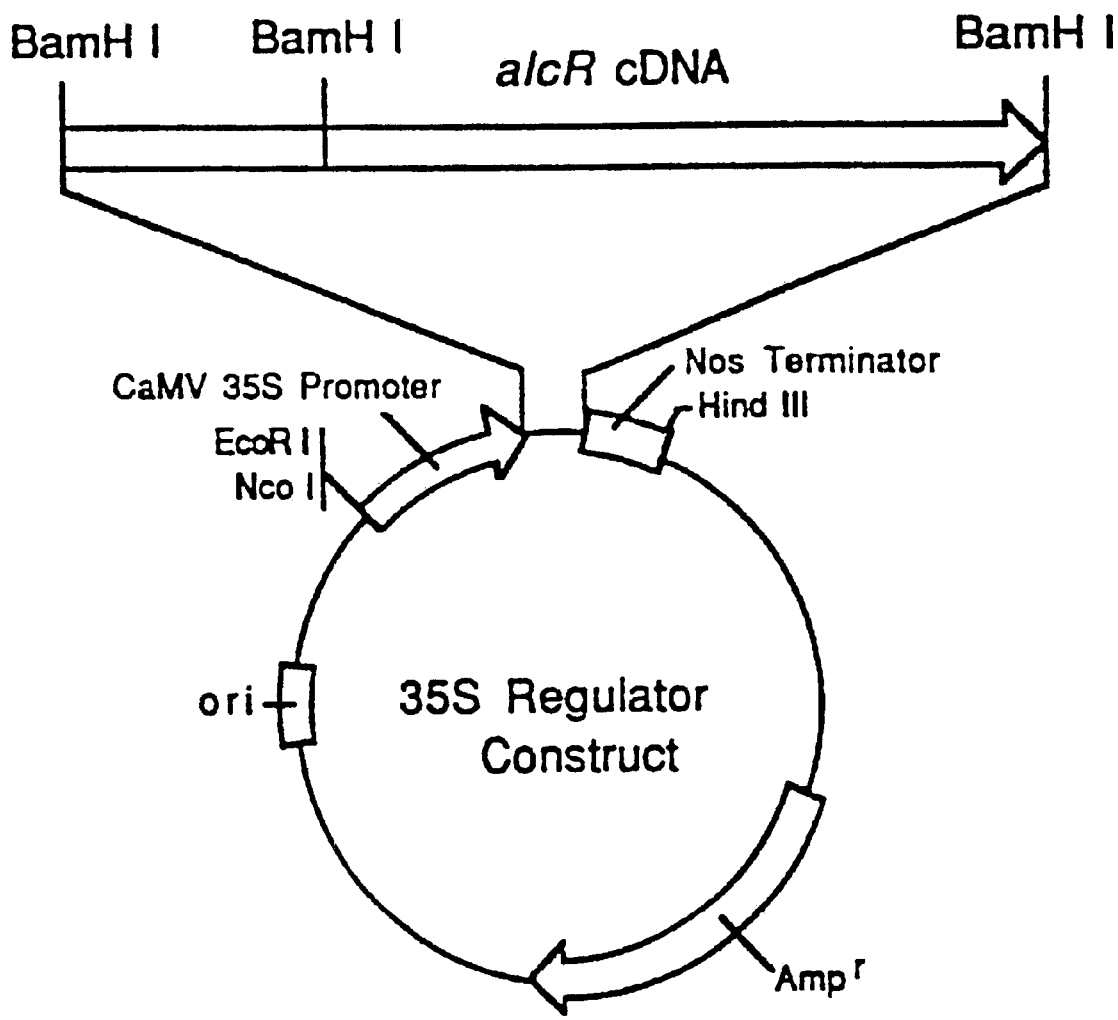

FIG. 1 illustrates the production of the 35S regulator construct by ligation of alcR cDNA into pJR1. Partial restriction of the alcR cDNA clone with BamHI was followed by electrophoresis in an agarose gel and the excision and purification of a 2.6 Kb fragment. The fragment was then ligated into the pJR1 vector which had been restricted with BamHI and phosphatased to prevent recircularisation. The alcR gene was thus placed under control of the CaMV 35S promoter and the nos 3' polyadenylation signal in this "35S-alcR" construct.

Figure 2B:
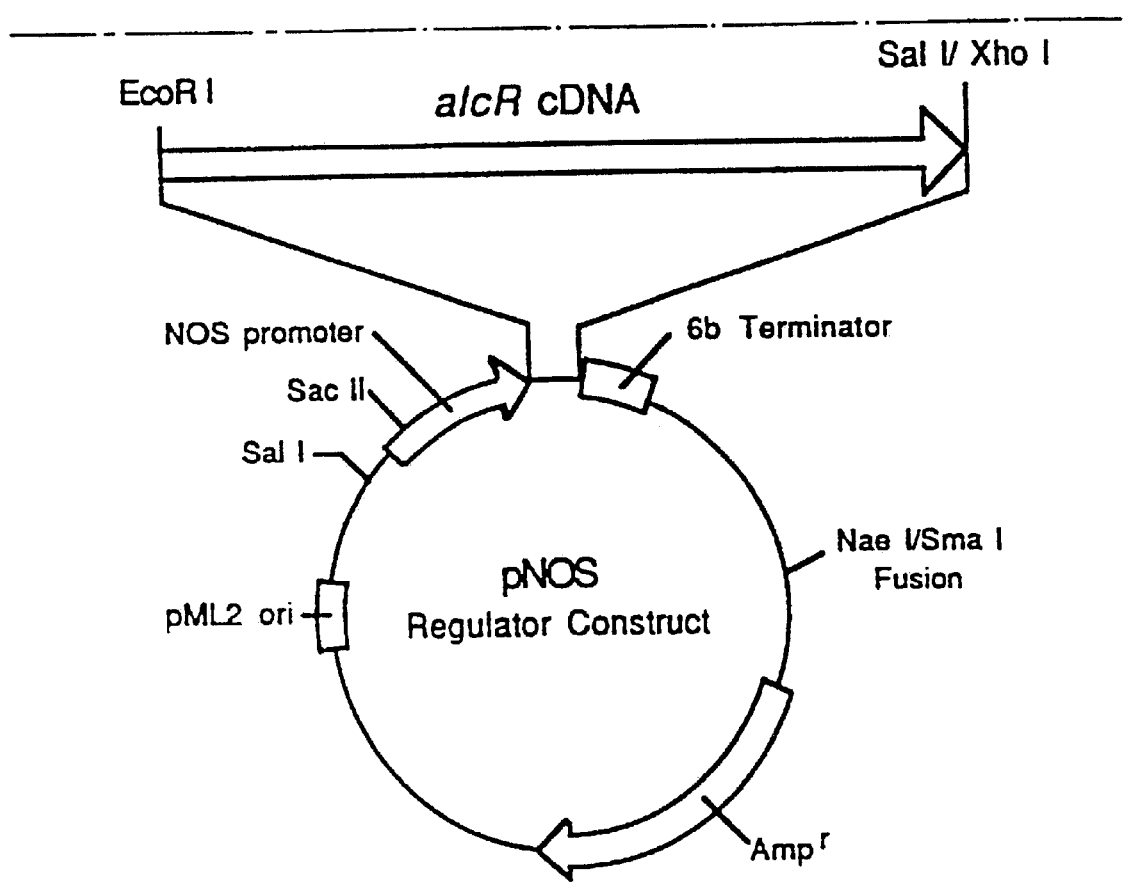

FIG. 2 illustrates the production of the pNOS regulator construct by ligation of alcR cDNA into pNOS. Restriction of the alcR cDNA clone with EcoRI and SalI was followed by electrophoresis and the excision and purification of a 2.8 Kb fragment. The pNOS vector was restricted with EcoRI and XhoI, phosphatased and then ligated to the 2.8 Kb alcR fragment. The alcR gene was thus placed under the control of the nos gene promoter and the nos 3' polyadenylation signal in this "nos-alcR" construct.

EXAMPLE 2

Production of the alcA-CAT Reporter Construct Containing the Chimeric Promoter The plasmid pCaMVCN contains the bacterial chloramphenicol transferase (CAT) reporter gene between the 35S promoter and the nos transcription terminator (the "35S-CAT" construct).

The alcA promoter was subcloned into the vector pCaMVCN to produce an "alcA-CAT" construct. Fusion of part of the alcA promoter and part of the 35S promoter created a chimeric promoter which allows expression of genes under its control.

Figure 3A:
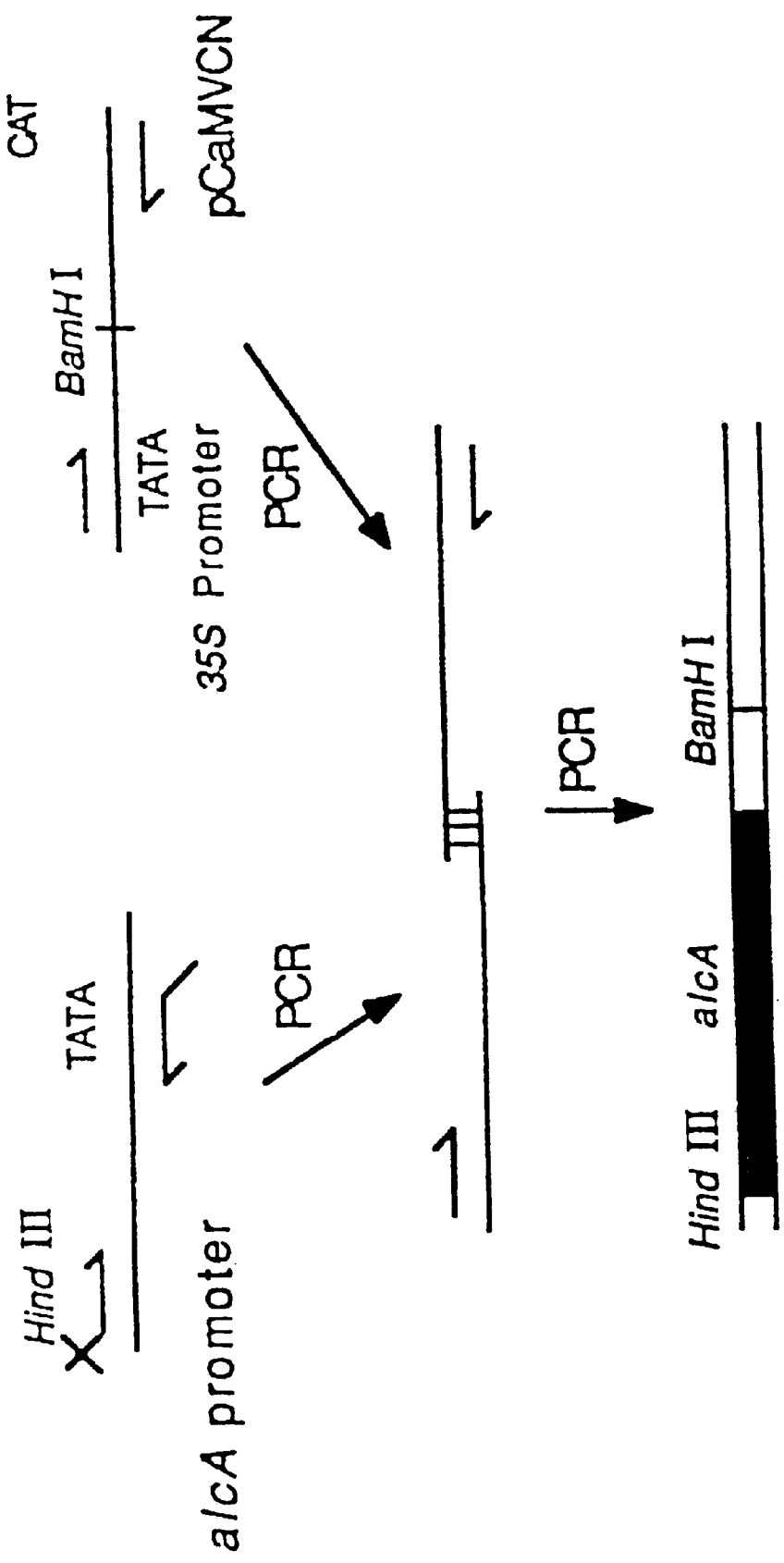
FIGS. 3A–3C show the production of the reporter construct.
Figure 3B:
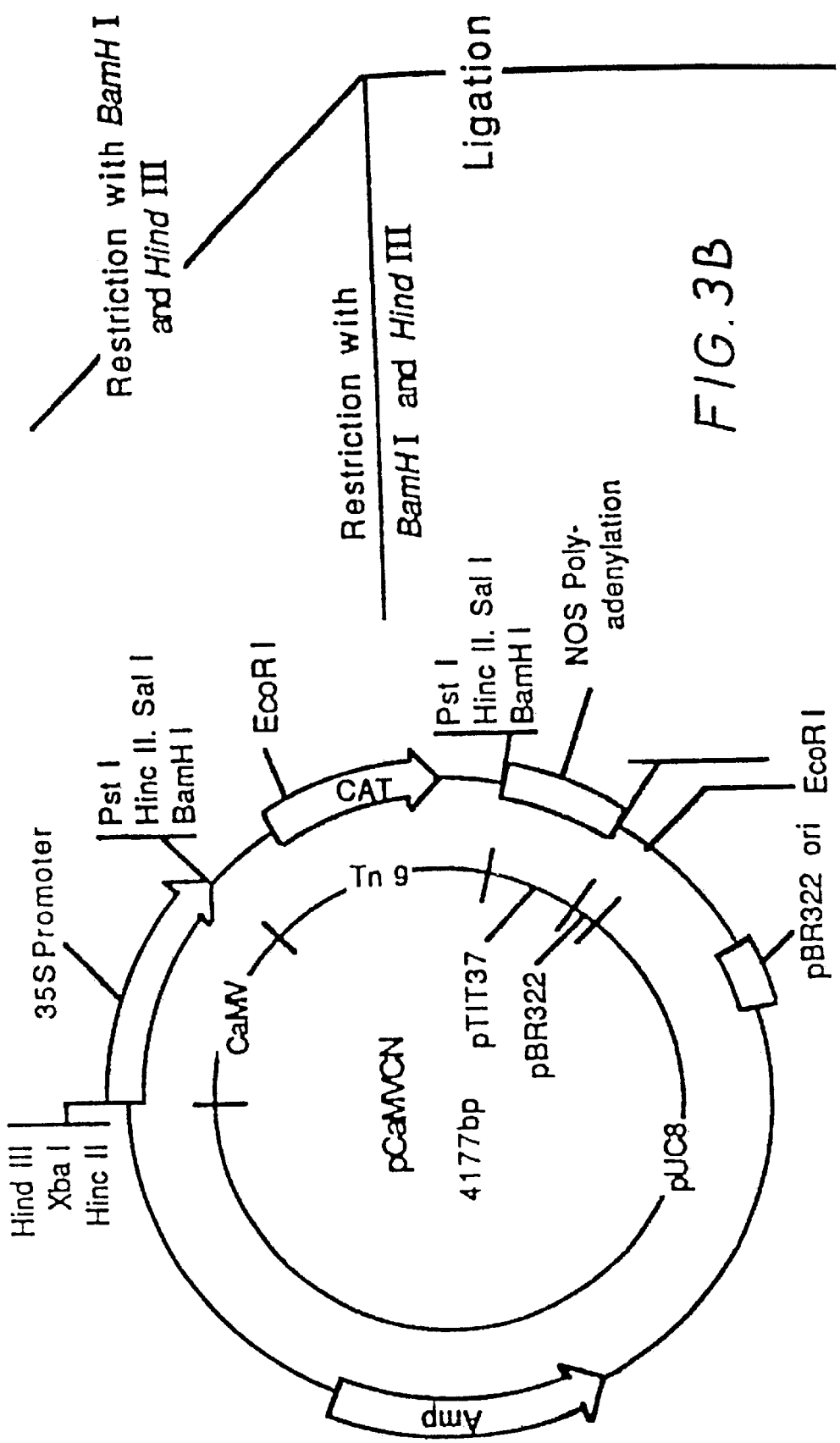
Figure 3C:
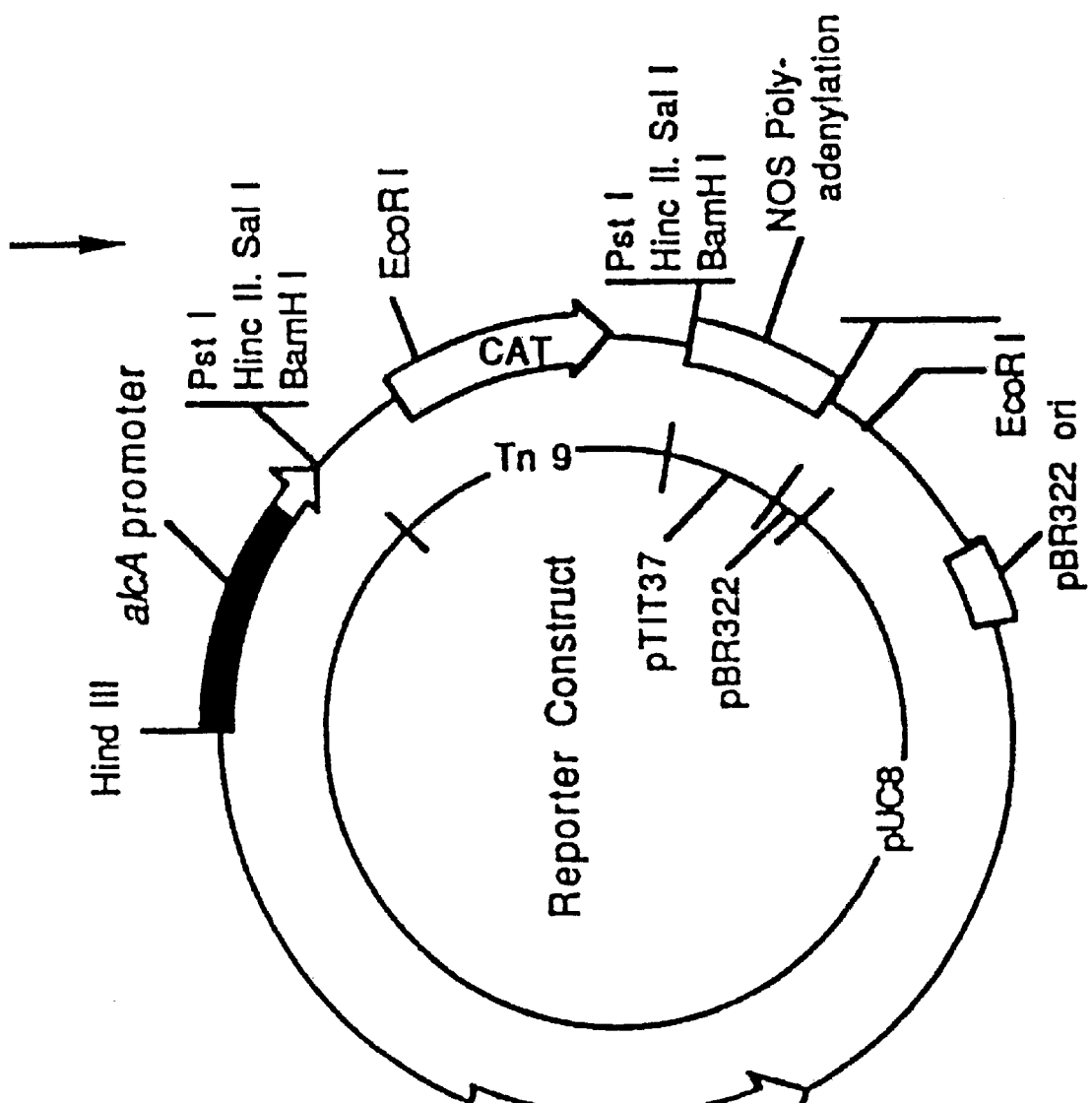

FIG. 3 illustrates the production of the reporter construct. The alcA promoter and the 35S promoter have identical TATA boxes which were used to link the two promoters together using a recombinant PCR technique: a 246 bp region from the alcA promoter and the 5' end of the CAT gene from pCaMVCN (containing part of the −70 core region of the 35S promoter) were separately amplified and then spliced together using PCR. The recombinant fragment was then restriction digested with BamHI and HindIII. The pCaMVCN vector was partially digested with BamHI and HindIII, then electrophoresed so that the correct fragment could be isolated and ligated to the recombinant fragment.

The ligation mixtures were transformed into *E coli* and plated onto rich agar media. Plasmid DNA was isolated by miniprep from the resultant colonies and recombinant clones were recovered by size electraphoresis and restriction mapping. The ligation junctions were sequenced to check that the correct recombinants had been recovered.

EXAMPLE 3

Expression in *Aspergillus nidulans*

The completed alcR and alcA constructs were transformed into *A nidulans* to test their functioning. Integration of the constructs into the genome is verified by Southern blotting of DNA fragments, while correct expression is shown by northern blotting to identify RNA transcripts.

Growth Conditions

*A nidulans* was maintained on complete or minimal media containing 1% agar. *A nidulans* mycelia was grown from conidial suspensions in supplemented minimal media with 1% glucose as the carbon source, and 10 mM ammonium tartrate as the nitrogen source for 16 hours, at 200 revs/min in an orbital incubator at 37° C. The mycelia was harvested by sieving through nylon fabric and washing with chilled distilled water. The mycelia was pressed dry between sheets of absorbent paper and frozen in liquid nitrogen. The mycelia could be stored at −70° C. if necessary.

Transformation of *A nidulans*

The *A nidulans* transformation procedure was developed from the methods of Ballance and Turner (1983) and Cambell E J et al. (1989, Curr. Genet, 16:53–56). Plasmids were transformed into *A nidulans* strains by the co-transformation method. A plasmid containing the argB gene or the *N crassa* pyr4 gene was used to complement the argB2 or pyrG89 mutation in *A nidulans*. Transformants were obtained by selecting transformed protoplasts on minimal media without the argB or pyr4 supplements. By adding a five fold excess of another plasmid with the complementing plasmid, some transformants were obtained which also contained a genomic copy of the other plasmid. Cellophane discs, 9 cm in diameter were placed onto petri dishes of complete medium. A conidial suspension was made up by scraping 1 $cm^2$ of conidia from a fresh confluent *A nidulans* plate and resuspending it into 3 ml of distilled water. The conidial suspension was spread onto 10 cellophane plates, 200 $\mu$l per plate, and incubated at 37° C. for 15 hours until the spores had germinated. The cellophane's were transferred to two petri dishes each containing 15 ml of novozyme 234 solution,(5 mg/ml novozyme 234 in 0.8 M $MgSO_4$, 10 mM $PO_4$ buffer pH 5.8) and incubated at 30° C. for 1.5–2 hours. The cellophane's were washed in 30 ml of solution A, (0.8 M $MgSO_4$ in 10 mM $PO_4$ buffer pH 5.8) and the wash solution and the novozyme solution was sieved through a glass scintillation funnel, size 1. The protoplasts were centrifuged at 3000 revs/min for 10 minutes and resuspended in 6 ml of solution B, (1.2 M sorbitol, 50 mM $CaCl_2$, 10 mM Tris pH 7.5). The protoplasts were centrifuged at 2500 revs/min for 5 minutes and resuspended in 6 ml of solution B and then centrifuged at 2500 revs/min for 5 minutes. The protoplast pellet was then resuspended in 400 $\mu$l of solution B. 50 $\mu$l aliquots of the protoplast suspension were transferred into plastic bijou's and up to 5 mg of plasmid DNA (1 mg/ml) was added. The ratio of the plasmids transformed was 5:1, (i.e., five times as much of the plasmid of interest was used compared to the transforming plasmid). 12.5 $\mu$l of solution C, (50% PEG 4000, 50 mM $CaCl_2$, 10 mM Tris pH7.5), was added to each bijou of protoplasts and the suspension was gently mixed. The cells were incubated on ice for 20 minutes and then 0.5 ml of solution C was added and mixed with the cells. Immediately, 1 ml of solution B was added, and the cells were mixed with 5 ml of precooled (55° C.) selection medium containing 1.2 M sorbitol and 10 mM sodium nitrate as the sole nitrogen source. An aliquot of untransformed protoplasts was added to selection medium as a control. The protoplasts were incubated at 30° C. overnight then at 37° C. for 2–3 days until conidiating colonies were obtained. Transformed colonies were tested for their markers on selective media before being experimented on.

Induction of *A nidulans* Mycelia

Conidial suspensions of *A nidulans* were grown in supplemented minimal medium containing 0.1% fructose as the carbon source, for 20 hours at 200 revs/min in an orbital incubator at 37° C. Inducing chemical was added to the mycelia at 20 hours and allowed to grow for a further 4 hours. The mycelia was harvested as before. Uninduced mycelia was allowed to grow for 24 hours in the medium described above.

Protein Extractions from *A nidulans* Mycelia 300 mgs of mycelia, frozen in liquid nitrogen, was ground in a chilled pestle and mortar with an equal amount of acid washed sand for 20 seconds. 1 ml of extraction buffer, (0.1 M Tris pH 7.5), was added and the mycelia ground for a further 30 seconds. Another 1 ml of extraction buffer was added and the mycelia was ground again for 30 seconds. 1 ml of the ground mycelia mixture was transferred into eppendorfs and centrifuged at 13,000 revs/min for 5 minutes in a microcentrifuge. The supernatant was transferred to new eppendorfs and the protein concentration estimated using the Bradford's assay.

DNA Extractions from *A nidulans* Mycelia 300 mgs of mycelia was ground in a precooled pestle and mortar in liquid nitrogen until a fine powder was obtained. The mycelia was transferred to a 30 ml corex tube containing 7 ml of DNA extraction buffer and then 7 ml of phenol was added and mixed. 7 ml of chloroform: iaa was added and the extraction mixture was gently mixed for 10 minutes. The mixture was centrifuged at 14,000 revs/min for 30 minutes and then the supernatant was carefully transferred into several 1.5 ml eppendorf tubes. The supernatant was extracted with an equal volume of phenol, then phenol/chloroform, then chloroform. 100 $\mu$l of heat treated $RNAse_{,}$(5 mg/ml), was added and incubated at 37° C. for 30 minutes. Two volumes of ethanol and 0.1 volumes of 3 M sodium acetate was added and mixed and incubated at room temperature for 10 minutes. The DNA was pelleted by centrifugation at 13,000 revs/min for 10 minutes in a microcentrifuge and then washed in 70% ethanol and dried at room temperature for 30–60 minutes. The DNA was redissolved in TE or sterile distilled water at a concentration of 1 mg/ml.

Results (A) The Regulator (alcR) Constructs

Experiments have established that the alcR regulator constructs function in *A nidulans*. The constitutive promoters drive expression of the alcR gene to produce regulator protein.

The alcR constructs were transformed into *A nidulans* strain alcR125 (alcR$^-$A$^+$) using the above standard techniques. Strain alcR125 is a null mutant strain which carries a point mutation in alcR and cannot express the regulator protein. Expression of the alcR gene introduced on the regulator construct was tested by assaying alcohol dehydrogenase I (ADH1), since the alcR gene product is known to switch on the alcA gene coding for ADH1. ADH1 activity was restored in the presence of inducer, demonstrating that the introduced alcR regulator construct was functional in *A nidulans*. The alcR gene product may also be assayed directly by Western blotting of proteins using antibodies raised against purified alcR gene product expressed in *E coli*. The transformed strain was back-crossed to the parent strain to determine whether the regulator construct had integrated heterologously into the genome. This experiment showed that the restoration of ADH1 activity was due to the presence of the regulator construct and not reversion of the point mutation in alcR125. As a control comparison, the alcR cDNA was transformed into *A nidulans* without an associated promoter.

Further details of these experiments are given below.

(i) The transformation of alcR125 *A nidulans* with the alcR cDNA regulator construct:

The alcR125, argB2 strain of *A nidulans* was co-transformed with the p35SalcR/pUC and pILJ16 plasmids using the PEG method. The p35SalcR/pUC plasmid contains the alcR cDNA between the 35S promoter and the nos transcription terminator. The pILJ16 plasmid contains a genomic copy of the argB2 gene from *A nidulans* and can complement argB2 mutations in *A nidulans*.

Five independent *A nidulans* transformants were obtained which were able to grow to wild type levels on media containing ethanol as the sole source of carbon. The ability of a strain to grow on ethanol-containing media is the phenotype of a functional alcR gene. The transformants varied in their ability to grow on ethanol, presumably the result of the genomic position of the alcR regulatory construct.

(ii) Back-crossing of the alcR+ transgenic *A nidulans* strains with an alcR+ wild type strain:

Two of the alcR+ transformants were back-crossed with an alcR+ wild type strain and the progeny tested for their ability to grow on ethanol-containing media. The alcR+ wild type strain was also wild type for spore colour. Two hundred of the progeny obtained from the mature cleistothesium were grown on ethanol-containing media and scored for their alcR phenotype. The ratio of alcR$^+$to alcR$^-$phenotype found in the progeny was 3:1. The ratio of the green to yellow phenotype in the same two-hundred progeny was found to be 1:1.

(iii) Back-crossing of the alcR+ transgenic *A nidulans* strains-with an alcR125 strain:

The above two alcR+ transformants were crossed with an alcR125 strain and the progeny obtained were scored for alcR phenotype. The alcR125 strain also had the panto mutation. Two hundred progeny were grown on ethanol-containing media and were found to exhibit an alcR$^+$to alcR$^-$ratio of 1:1. The ratio of the panto mutation to wild type gene was also found to be 1:1.

(B) The Chimeric Promoter

The generation of stably transformed wild type *A nidulans* with the alcA-CAT reporter construct established that the chimeric promoter is operative in *A nidulans*. Functioning of the alcA chimeric promoter introduced on the reporter construct was tested by assaying expression of the CAT gene. Initiation of CAT gene expression under inducing conditions demonstrated that the chimeric alcA:35S promoter was functioning correctly.

The alcA-CAT reporter construct was transformed into a wild type *A nidulans* strain (alcR$^+$A$^+$). The wild type strain has a normal alcR gene producing the regulator protein necessary for activation of the alcA promoter in the presence of inducer.

Stably transformed *A nidulans* was obtained by co-transforming a pyrG89 strain with the pDJB3 and palcA-CAT/pUC plasmids using the PEG method. Plasmid palcA-CAT/pUC contains the CAT reporter gene between the alcA:35S chimeric promoter and the nos transcription terminator. Two independent transformants (GA2-1 and GA2-5) were obtained which contained uninterrupted copies of the alcA-CAT construct. This was shown by probing genomic DNA, restricted with HindIII, with the 0.7 kb SalI fragment of the CAT gene.

Figure 4:
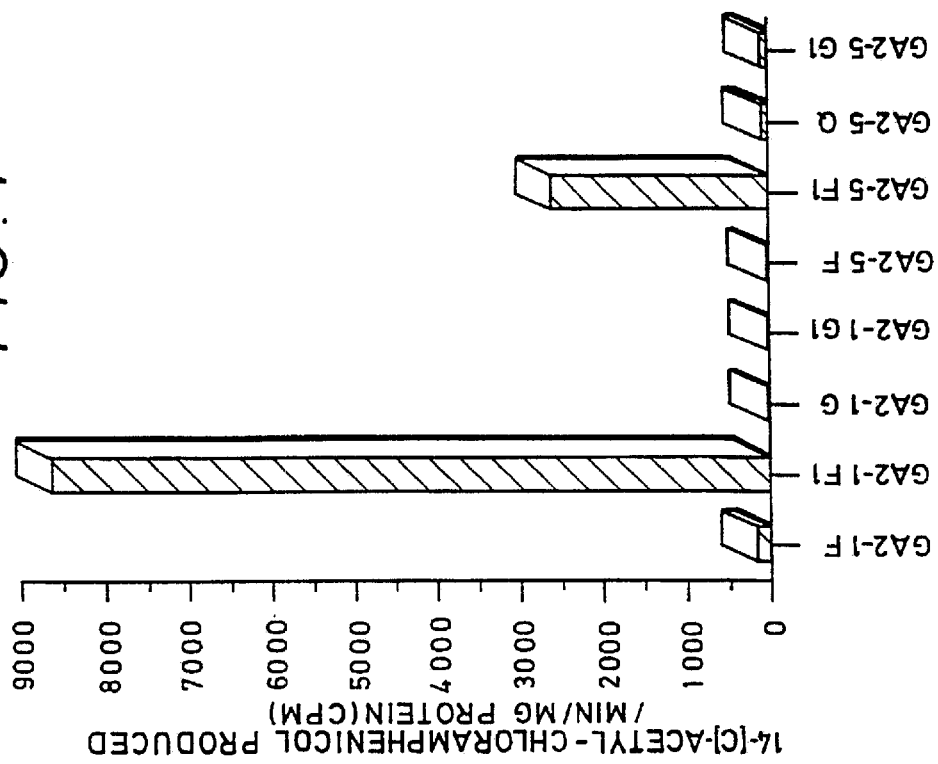
FIG. 4 is a graph showing CAT expression from *A nidulans* alcA-CAT transformants.

The CAT activity of the alcA-CAT *A nidulans* transformants was measured when they were grown under a variety of conditions. FIG. 4 is a graph showing CAT expression from the GA2-1 and GA2-5 transformants (wild type with alcA-CAT construct) growing in 0.1% fructose (F) or 1% glucose (G) in the absence or presence of 50 mM ethyl methyl ketone as inducer (I). The CAT activity of the alcA-CAT reporter construct in the transformed *A nidulans* strains was found to be high only when the transformants were grown in 0.1% fructose and in the presence of inducer. The induction of CAT was prevented when the transformants were grown in 1% glucose even in the presence of inducer indicating the carbon catabolyte repression function of the alcA promoter was retained. The two transformants, GA2-1 and GA2-5, exhibited different CAT induction abilities, most likely due to the differing genomic positions of the alcA-CAT reporter constructs.

Figure 5:
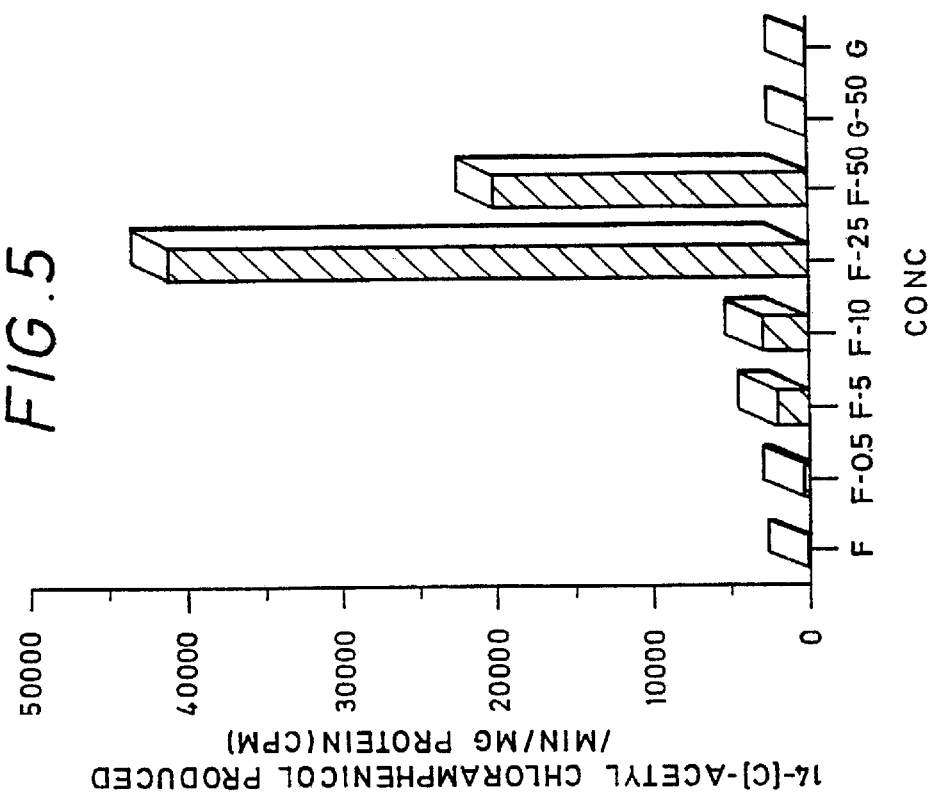
FIG. 5 is a graph showing CAT expression from an *A nidulans* alcA-CAT transformant against cyclohexanone concentration.

Transformant GA2-1 was found to be over three times more inducible than transformant GA2-5 when 50 mm ethyl methyl ketone was used as the inducer. Cyclohexanone was found to induce CAT expression in the GA2-1 transformant. A concentration curve showed that cyclohexanone had an optimal inducing ability on the GA2-1 transformant when used at 25 mM. FIG. 5 is a graph showing the effect of cyclohexanone concentration (mM) on CAT expression in the transformant GA2-1 growing in 0.1% fructose (F) or 1% glucose (G).

Figure 6:
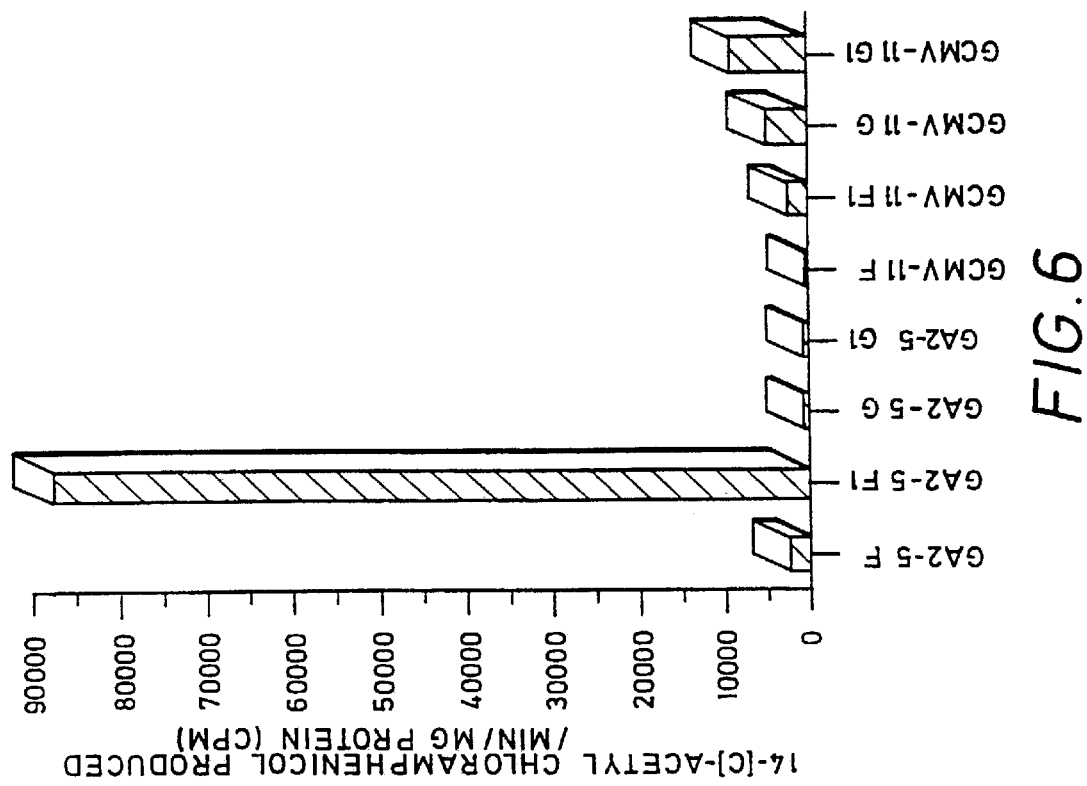
FIG. 6 is a graph showing CAT expression from an *A nidulans* alcA-CAT transformant and a 35S-CAT transformant.

Stably transformed *A nidulans* was also obtained by co-transforming the pCaMVCN plasmid (35S-CAT construct) with the pDJB3 plasmid into the wild type strain using the PEG method. The plasmid pDJB3 contains the pyr4 gene from *N crassa*, which compliments the pyrG89 mutation in *A nidulans*. One independent *A nidulans* transformant (GCMV-11) was obtained which was found to contain the 35S-CAT construct in uninterrupted form when genomic DNA, restricted with HindIII, was probed with the 0.7 kb SalI fragment of the CAT gene, in a Southern hybridisation. Digestion of the genomic DNA with XhoI and hybridization with the 0.7 kbp SalI fragment of the CAT gene revealed multiple copies of the 35S-CAT sequence in the transformant. The function of the 35S promoter was tested by measuring the CAT expression obtained from the 35S-CAT *A nidulans* transformant. FIG. 6 is a graph showing CAT expression from the GA2-5 ransformant (wild type with alcA-CAT construct) and the GCMV-11 transformant (wild type with 35S-CAT construct) growing in 0.1% fructose (F) or 1% glucose (G) in the absence or presence of 50 mM ethyl methyl ketone as inducer (I). The expression of CAT in the 35S-CAT *A nidulans* transformant was found to be at a much lower level than that of the alcA-CAT *A nidulans* transformants.

(C) The Gene Expression Cassette

The following experiments established that the gene expression cassette (comprising the alcR regulator construct and the alcA reporter construct) functions in *A nidulans*.

The alcA construct was transformed alone into mutant *A nidulans* strain alc500 (alcR$^-$A$^-$). This mutant contains a deletion extending over both the alcR and the alcA genes: hence the reporter protein is not naturally present. There was a very low rate of CAT gene expression. Thus, the alcA construct was not functional in the absence of alcR regulator protein. As a control comparison, the pCaMVCN plasmid (containing the CAT gene under the control of the constitutive CaMV 35S promoter) was transformed into the *A nidulans* deletion strain alc500.

The regulator alcR construct and the alcA reporter construct were then co-transformed into the alcR$^-$A$^-$deletion strain alc500. Any expression of the CAT reporter gene is induced by the alcR regulator protein produced by the regulator construct, without interference from a wild-type regulator protein. Transformants were grown either on fructose or glucose and subjected to inducing conditions (4 hours in the presence of ethyl methyl ketone, EMK) or non-inducing conditions (in the absence of EMK). Results of the CAT assays are shown in Table 1.

TABLE 1

CAT assays

| EMK (INDUCER) | CARBON SOURCE | µg CAT/mg protein |
|---|---|---|
| YES | fructose | 5.67/4.58 |
| NO | fructose | 0.12/0.08 |
| YES | glucose | 0.01/0.00 |
| NO | glucose | 0.07/0.00 |

The results show that the CAT reporter gene is correctly expressed under conditions which would normally induce expression of the ADH1 gene: that is, growth on fructose in the presence of inducer.

Growth on glucose results in poor expression of the CAT reporter gene. Glucose is known to repress ADH1 expression in wild type A nidulans strains.

The alcA:35S chimeric promoter is inducible. The promoter drives expression of the CAT reporter gene when the regulator protein and inducer are present. Thus the gene expression cassette (comprising the alcR and alcA constructs) is functional and chemically-inducible.

Similar studies were conducted using a construct with the CaMV promoter alone fused to CAT. In these experiments, low levels of CAT activity were detected following growth on glucose and were not induced by treatment with inducer.

Expression vectors lacking the alcR regulator gene were also transformed into A nidulans with the alcA constructs. There was only a low level of CAT gene expression, showing that it is the regulator gene which controls the expression of the reporter gene, through the action of the regulator protein on the alcA fusion promoter.

EXAMPLE 4

Expression in Plants: Transient Expression in Maize Protoplasts

The alcA-CAT and 35S-alcR constructs were introduced into maize protoplasts to determine CAT expression in transient assays after incubation in the present of ethanol.
Isolation of Protoplasts from Maize Maize protoplasts were prepared from a suspension culture of Black Mexican Sweet (BMS) cells using the following method.

The cells were harvested two days after a subculture and digested in E1 enzyme solution, (2.0% cellulase RS, 0.2% pectolase Y23, 0.5M mannitol, 5 mM CaCl2.2H2O,0.5% MES pH5.6). 10 ml of enzyme solution was added to each gramme of tissue and incubated for 2 hours a 25° C. in dim light while gently rotating. The digestion mixture was sieved sequentially through 250 µm and 38 µm sieves, rinsing with wash buffer (0.358 M KCl, 1.0 mM NH$_4$.NO$_3$, 5.0 mM CaCl$_2$.2H$_2$0, 0.5 mm KH$_2$PO$_4$ pH4.8). The protoplasts were centrifuged at 700 revs/min for 3.5 minutes and resuspended in 30 ml of wash buffer twice. The protoplasts were counted using a Fuchs-Rosenthal haemocytometer. The protoplasts were then used for transient assays.

Introduction of DNA into Maize Protoplasts

DNA was introduced into the protoplasts by the PEG uptake procedure. The protoplasts were resuspended at 2×10$^6$/ml in MaMg medium and aliquoted out at 0.5 ml per treatment. The protoplasts were heat shocked at 45° C. for 5 minutes, then allowed to cool to room temperature for 10 minutes. A standard quantity of DNA, (at 1 mg/ml), was added to the protoplast aliquots. 25 µg of the control plasmid was added to an aliquot of protoplasts; the amount of other plasmids added varied according to their size. 0.5 ml of PEG solution at 45° C. was added and mixed gently with the protoplasts. The protoplasts were incubated at room temperature for 20 minutes then 5 ml of KCl solution was added, 1 ml at a time. The protoplasts were incubated at room temperature for 10–15 minutes and then were centrifuged at 700 revs/min for 3.5 minutes. The supernatant was removed and each sample was resuspended in 1.5 ml of BMS+9% mannitol and incubated at 25° C. in the dark for 22 hours.

The maize protoplasts were transformed with the following constructs:
(a) CaMV35S promoter fused to the chloramphenicol acetyl transferase gene (35S-CAT);
(b) alcA:35S chimeric promoter fused with the CAT gene (alcA-CAT);
(c) 35S promoter fused to the alcR gene, plus the alcA-CAT construct (alcA-CAT/35S-alcR);
(d) 35S promoter fused to maize intron I and the alcR gene, plus the alcA-CAT construct (alcA-CAT/35S-I1-alcR). [Intron I from the maize adhI gene has previously been shown (Callis et al, 1987, Genes and Development, 1:1183–1200) to increase expression from a number of genes in maize cells].

Each plasmid combination was introduced into the protoplasts in three separate aliquots.
Transient CAT Expression Assays Following incubation for 22 hours in media containing 17 mM ethanol as an inducer of the alcR gene product, protoplasts were harvested and proteins extracted as follows.

The protoplast samples were transferred to eppendorfs and centrifuged at 13,000 revs/min for 3 minutes. 100 µl of 0.1 M Tris pH7.8 was added and the cells were resuspended using a micro pipette. The eppendorfs were vortexed for 30 seconds and then centrifuged again at 13,000 revs/min for 5 minutes. 50 µl of the supernatant was used to measure the CAT activity and the rest to estimate the protein concentration using the Bradford's method.

CAT activity was measured in samples of the protein extract. CAT assays were undertaken according to the Dupont method, where a scintillation counter was used to measure transfer of [$^{14}$C] acetyl chloramphenicol from the protein extract into an immiscible scintillation fluid over time.

Figure 7:
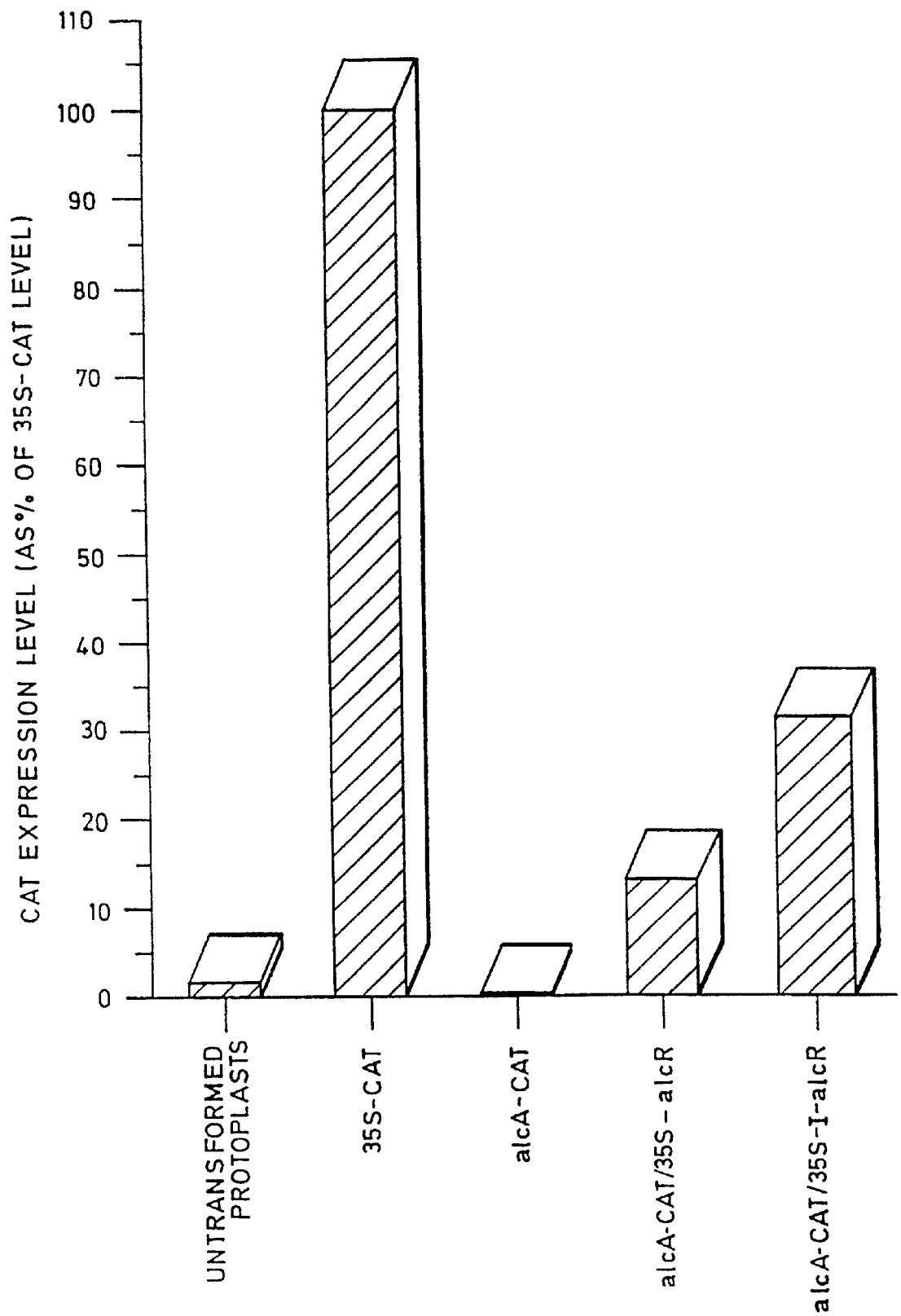
FIG. 7 is a graph showing relative CAT expression levels in maize protoplasts.

50 µl of protein extract was put in a plastic disposable scintillation vial, together with 200 µl of 1.25 mM chloramphenicol in 100 mM Tris pH7.8, and 0.1 µCi of [$^{14}$C] acetyl CoA. 5 ml of Econofluor, (950 ml/L toluene and 50 ml/L scint 7) was gently overlaid onto the reaction mixture and the vials were capped. The vials were counted (cpm) sequentially in a scintillation counter for 30 seconds for a period of 1–2 hours. The cpm values of the samples were plotted against time and the gradient taken as a measure of the CAT activity of the sample. The protein concentrations of the samples were measured using Bradford's method. The CAT activities of the samples were expressed as 14-[C]-acetyl chloramphenicol produced per minute per mg of protein.
Results The data from this experiment are shown in FIG. 7. CAT gene expression is given as a percentage of the CAT activity observed in cells transformed with the 35S-CAT construct (production of CAT under control of a constitutive promoter). The CAT activity from the 35S-CAT construct was expressed as 100% in order to compare results from separate batches of protoplasts. The expression from untransformed protoplasts is also shown.

Cells containing the alcA-CAT construct alone showed a similar level of CAT activity as present in control cells containing no DNA (the untransformed protoplasts).

Cells containing the alcA-CAT and the regulator constructs (35S-alcR and 35S-I1-alcR) show levels of CAT expression that are 7-fold and 16-fold higher respectively than cells containing the alcA-CAT gene alone. This establishes that expression of the CAT gene from the alcA:35S promoter in maize protoplasts incubated in media containing 17 mM ethanol (as the inducer) is dependent on the presence of the alcR gene. Also there is an apparent increase in CAT expression in the presence of the 35S-I1-alcR construct, presumably due to a higher level of expression of alcR mediated by the inclusion of maize intron I. The 35S-I1-alcR construct increases CAT expression from the alcA-CAT construct from 13% to 31% of that from the 35S-CAT construct.

Figure 8:
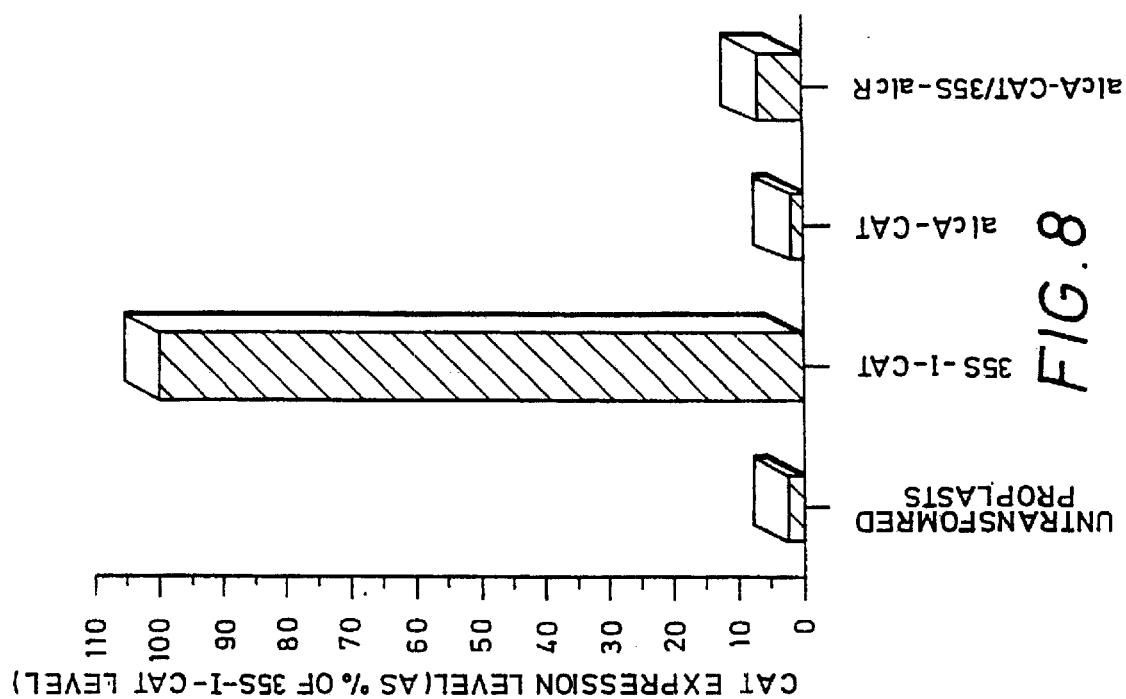
FIG. 8 is a graph showing relative CAT expression levels in maize protoplasts.

Further experiments with maize protoplasts have shown that the plant gene expression cassette is functioning correctly. For example, FIG. 8 is a graph showing the effect of the 35S-alcR regulator construct on CAT expression from the alcA-CAT construct in the presence of 17 mM ethanol. A 35S-I1-CAT construct was used as the positive control in this experiment.

EXAMPLE 5

Time Course of Expression in a Stably Transformed Tobacco Plant

Construction of Tobacco Transformation Vectors

Bin19 derivatives of the alcA-CAT construct and 35S-alcR/alcA-CAT construct were produced using standard procedures. Bin19 is a known plant transformation vector (Bevan, 1984, Nucleic Acids Research 12, 8711–8721).

The plasmid palcA-CAT/BIN contains the CAT reporter gene between the alcA:35S chimeric promoter and the nos transcription terminator. It was constructed as follows: The 1.4 kbp HindII fragment from from the alcA-CAT/pUC plasmid (containing the alcA:35S fusion promoter, the CAT gene and the nos transcription terminator) was cloned into the HindII site of the pJR1i/BIN19 vector. Transformed colonies were transferred to nylon membrane and were probed with the alcA-CAT sequence. Positive colonies were shown to be correct when miniprepped plasmid DNA digested with HindIII gave a 1.4 kbp fragment.

The plasmid p35SalcR-alcA-CAT/BIN contains the alcR cDNA between the 35S promoter and the nos transcription terminator, and the CAT reporter gene between the alcA:35S chimeric promoter and the nos transcription terminator. It was constructed as follows: Plasmid 35S-alcR/pUC was fully digested with HindIII and partially digested with EcoRI. The 3.5 kbp fragment was isolated and cloned into the pJR1i/BIN19 vector which had been restricted with EcoRI and HindIII. The 1.4 kbp HindIII fragment containing the alcA-CAT sequence from palcA-CAT/pUC was then cloned into the HindIII site in the 35S-alcR/JR1i/BIN plasmid. The correct plasmid was shown to contain the 1.4 kbp HindIII fragment form the alcA-CAT sequence, and the 3.0 kbp and 0.5 kbp EcoRI fragments from the 35S-alcR sequence. A 3.5 kbp partial EcoRI/HindIII fragment could be seen in the same digest. The orientation of the alcA-CAT sequence to the 35S-alcR sequence in the final plasmid is estimated to be head to tail.

Transformation of Agrobacterium tumefaciens

The disarmed Agrobacterium tumefaciens strain LBA4404 (pAL4404)(Hoekema et al, 1983, Nature 303, 179–180) was transformed with the above vectors using the freeze-thaw method. A single colony was grown up in 40 ml of LB medium at 28° C. in an orbital incubator at 200 revs/min overnight until the culture reaches an O.D.$_{580}$ of 0.5–1.0. The cells were resuspended in 1 ml of ice cold 20 mM $CaCl_2$ solution, and then dispensed into prechilled eppendorfs, 100 µl per tube. DNA was added to the cells, 0.1 µg/100 µl of cells, and then the cells were frozen in liquid nitrogen. The cells were then thawed at 37° C. in a water bath for 5 minutes. 1 ml of LB medium was added to each tube and the cells were incubated at 28° C. for 2–4 hours with gentle shaking to allow the bacteria to express the antibiotic resistance genes. The cells were centrifuged for 30 seconds at 13,000 revs/min in a microcentrifuge and the supernatant was discarded. The cells were resuspended in 100 µl of LB medium. The cells were spread onto LA agar plates containing 50 µg/ml kanamycin, or other antibiotic selection afforded by the introduced plasmid. The plates were incubated at 28° C. for 2 days, when colonies were likely to appear.

Plasmid Minipreps from Agrobacterium tumefaciens

Single colonies were grown in 20 ml of LB medium containing antibiotic as the selective agent overnight at 28° C. in an orbital incubator. The cells were centrifuged at 3000 revs/min for 5 minutes and the pellet was resuspended in 0.5 ml of miniprep solution, (5 mg/ml lysozyme in 50 mM glucose, 10 mM EDTA, 25 mM Tris-HCl pH 8.0). The cells were incubated on ice for an hour, and then 1 ml of alkaline SDS (0.2 M NaOH, 1% SDS) was added. After incubation on ice for 10 minutes, 0.75 ml of 3 M sodium acetate was added, and the mixture was left on ice for 30 minutes. The lysis mixture was centrifuged at 15,000 revs/min for 10 minutes at 4° C., and the supernatant was transferred to 15 ml corex tubes. 5 ml of cold ethanol was added and the tubes were stored at −70° C. for 30 minutes. The tubes were then centrifuged at 15,000 revs/min for 15 minutes at 4° C. and the supernatant was removed. The pellet was dissolved in 0.5 ml of T.E. and transferred to eppendorfs. The DNA solution was extracted with an equal volume of phenol/chloroform three times and once with an equal volume of chloroform. The DNA was precipitated by adding 1 ml of ethanol and incubating at −70° C. for 30 minutes. After centrifugation at 13,000 revs/min for 15 minutes in a microcentrifuge the DNA pellet was washed with 70% ethanol, dried at room temperature for a few minutes, and redissolved in 50 µl T.E. 20 µl of DNA solution was used per restriction digest. Generally, a 2–3 fold increase in restriction enzyme and at least 4 hours digestion was required for the Agrobacterium DNA to be digested adequately.

Tobacco Transformations

Transgenic tobacco was generated by the leaf disc method using transformed Agrobacterium tumefaciens. About 20 tissue culture grown plats were required per transformation. The plants were about 3–4 weeks old and were grown on M.S medium without antibiotics. All manipulations were carried out in sterile hoods using sterile implements.

Leaves were cut from the tissue culture plants, placed on NBM medium in petri dishes, and incubated overnight in a plant growth room. The transformed Agrobacterium strain was grown up overnight in 100 ml of LB containing kanamycin at 50 µg/ml. The next day the culture was centrifuged at 3000 revs/min for 10 minutes and resuspended in an equal volume of MS solution. 20 ml of Agrobacterium solution was placed in 9 cm petri dishes. Leaf discs were made form the leaves, using a sterile scalpel, and were put into the Agrobacterium solution in the petri dishes for 20 minutes. The leaf pieces were then transferred to the NBM plates and incubated overnight in a plant growth room. After 48 hours the leaf discs were transferred to NBM medium containing carbenicillin at 500 µg/ml and kanamycin at 100 µg/ml in neoplant pots. The pots were incubated in a plant growth room for 4–6 weeks. Shoots emerging from callous tissue were transferred to MS medium containing carbenicillin at 200 µg/ml and kanamycin at 100 µg/ml in neoplant pots, (7 to a pot). After 3 weeks, shoots that had rooted were transferred to fresh MS medium and grown on until they were about 5 cm in height. Extra cuttings-were taken at this stage. The plants were then transferred to compost in 13 cm pots and sealed in polythene bags to prevent dehydration for the first few weeks.

Induction of Transgenic Tobacco Plants

Cyclohexanone was applied to the plant leaves as a paint. The cyclohexanone paint consisted of a 10% solution of 950 g/L cyclohexanone, 35 g/L syperonic NDE 1800, 16.5 g/L Tween 85 in thickener. Both surfaces of the leaf were applied with paint at 100 µl solution per 16–25 cm$^2$ of leaf surface, on days 0 and 2. Leaf tissue was harvested prior to inducer application and at appropriate times after the second application of paint. 1 cm$^2$ of leaf tissue was removed with a sterile scalpel, put in an eppendorf, and immersed in liquid nitrogen. CAT assays were undertaken within 4 hours of leaf sampling.

Protein Extractions from Tobacco Leaf Tissue

The leaf tissue was allowed to defrost at room temperature for several minutes after storage in liquid nitrogen. A sterile micropestle was used to grind the leaf tissue in the eppendorf for 30 seconds and then 100 µl of 100 mM Tris pH 7.8 was added. The plant mixture was then vortexed for 20 seconds and centrifuged at 13,000 revs/min for 5 minutes. The supernatant was transferred to a new eppendorf. 50 µl of leaf extract was used for a CAT assay and the rest was used to determine the protein concentration wit the Bradford's method.

CAT Assays

CAT assays were undertaken according to the Dupont method as described in Example 4.

Results (A) Generation of Stably Transformed Tobacco with the alcA-CAT Reporter Construct The plasmid palcA-CAT/BIN was used to produce transgenic tobacco plants. Forty-four independent tobacco transformants were obtained, of which twenty-three were shown to contain the alcA-CAT construct when genomic DNA was amplified using PCR with the oligo's C3 and A3. Four plants were shown to contain the construct in uninterrupted form when genomic DNA, restricted with HindIII, was probed with the 0.7 kb SalI of the CAT gene.

(B) Generation of Stably Transformed Tobacco with the alcA-CAT Reporter and the alcR-cDNA Regulator Cassette The plasmid p35SalcR-alcA-CAT/BIN was used to produce transgenic tobacco plants. Twelve independent tobacco transformants were obtained, and analysed for the presence of the alcR regulatory and alcA-CAT reporter constructs using PCR. Ten of these plants were shown to contain the alcR regulatory construct using the oligos, L4 and L6, in PCR. One of those plants, D3, was shown to contain the alcA-CAT reporter construct by PCR using the oligos, A3, and C3.

(C) Analysis of the CAT Expression Found in the Transgenic Tobacco Before Induction Leaf tissue was used to measure the CAT activity of the transgenic plants. All of the alcA-CAT transgenic plants were found to exhibit low CAT activity levels. The CAT expression levels varied between individual plants but none were found to have higher CAT expression levels than those of the control tobacco plants. None of the alcR regulatory/alcA-CAT reporter transgenic tobacco plants were found to have high CAT expression levels. The CAT activities were low and were not above those of the control tobacco.

(D) The Effect of Cyclohexanone on the CAT Activities of the Plants

None of the alcA-CAT transgenic plants were found to have high CAT expression levels after the application of the cyclohexanone paint to the leaves. The CAT expression levels varied between plants, but none were found to have expression levels higher than those of the control tobacco plants. Of the 35S-alcR/alcA-CAT transgenic tobacco plants, one, D3, was found to exhibit a high CAT expression level after application of cyclohexanone to its leaves. The level was much higher than that found in control tobacco plants.

(E) Time Course Experiment Following CAT Activity after Application of Cyclohexanone The plant known as D3 was shown by PCR to contain both the alcR regulatory and the alcA-CAT reporter gene fusions (ie the entire gene expression cassette).

This experiment was a time course analysis of plant D3 compared with a plant containing only the alcA-CAT construct (known as S34) and with an untransformed control (known as T1), following treatment with a formulated leaf paint containing the alcR inducer, cyclohexanone. The latter has been shown previously to be a potent inducer of ADHI expressed from the alcA gene in Aspergillus cells.

Figure 9:
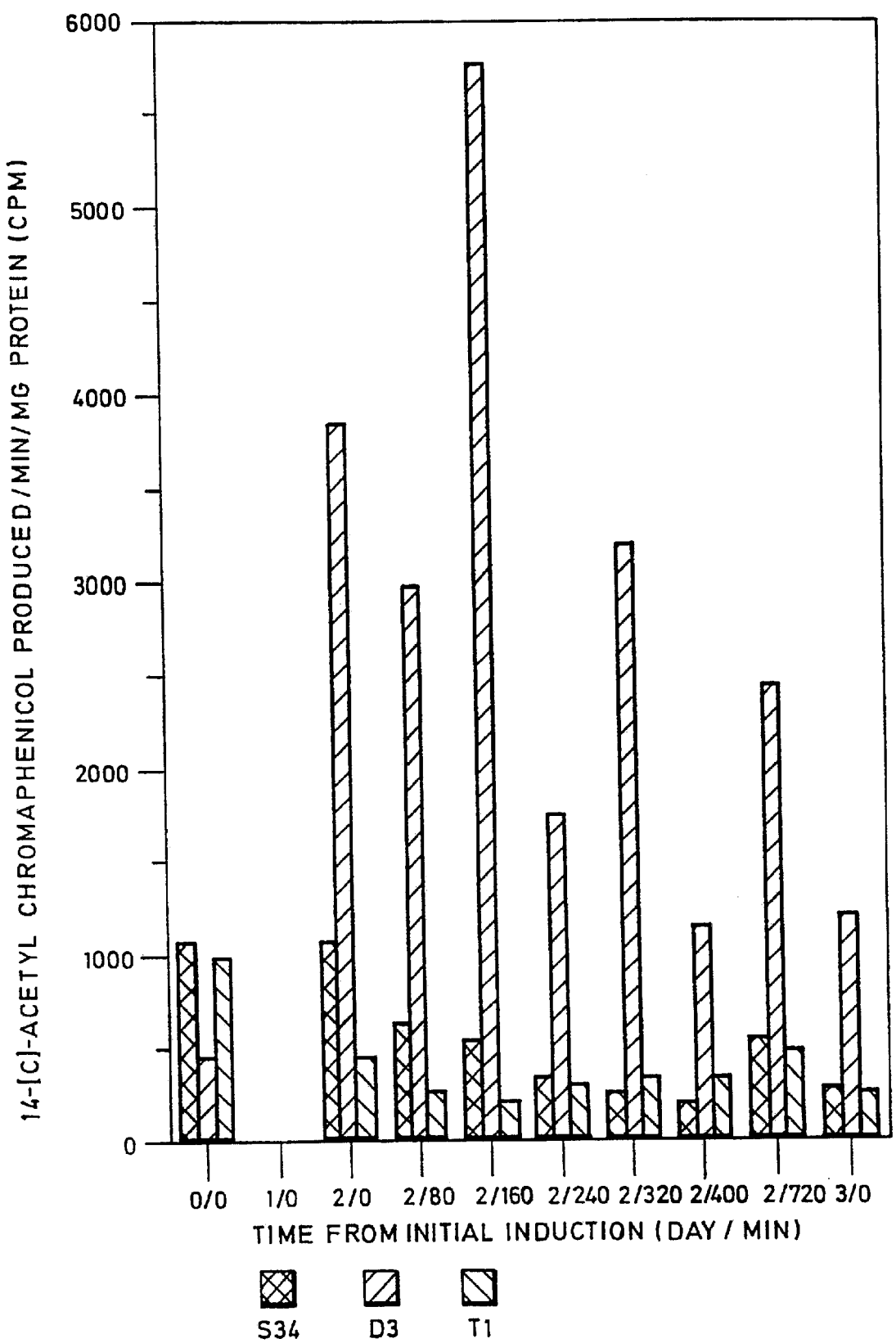
FIG. 9 is a graph showing relative CAT expression levels in stably transformed tobacco.

The data obtained from this analysis are shown in FIG. 9: at each time point, results are given in the order S34:D3:T1. Leaves were treated with cyclohexanone leaf paint on day 0 and day 2. Samples of leaf tissue were taken immediately prior to each treatment (0–0 and 2–0 in FIG. 9) and thereafter at seven intervals up until day 3. Protein extracts were made from the leaf samples and CAT activity determined in the samples using the diffusion assay described above.

Following painting with cyclohexanone, CAT activity increases in the leaves of plant D3 (containing the 35S-alcR/alcA-CAT genes), reaching a peak at 160 minutes after the second inducting treatment, and thereafter declines (FIG. 9).

In contrast, treatment with cyclohexanone had no effect on the untransformed plant (T1) or the plant containing only the alcA-CAT gene (S34). In these plants, CAT activity remained at about 5–20% of the maximum activity seen in the 35S-alcR/alcA-CAT leaves.

This experiment established that in stably transformed plants containing the gene expression cassette 35S-alcR/alcA-CAT, high levels of expression of the reporter gene (CAT) are only obtained in the presence of the alcR regulator gene product and following exogenous treatment with the inducing chemical, cyclohexanone. The inducer cyclohexanone has no effect on CAT gene expression plants containing alcA-CAT alone.

(F) The Effect of Wounding on the CAT Expression in the Plants

Leaves of the plants were lacerated with a razor blade and the effect on CAT expression was measured. Samples of leaf tissue taken 240 minutes after laceration showed no increase in CAT activity in any of the plants (ie no induction of gene expression). Therefore wounding was found to have no effect on the alc expression cassette by this method.

(G) The Effect of Iso-propanol on the CAT Expression of the Plants

Iso-propanol is a weak inducer and a substrate for alcA, whereas cyclohexanone is an inducer but not a substrate (Creaser et al, 1984, Biochem J, 255:449–454). Iso-propanol has no apparent effect on the alc expression cassette.

The leaves of the plants were painted with a 10% iso-propanol solution at 0 and 60 minutes and the CAT expression of leaf samples was measured at 240 minutes. The CAT expression found in the alcA-CAT and alcA-CAT/35S-alcR transgenic plants at 0 minutes was low as it was in the control untransformed tobacco plants. After 240 minutes no significant increase in CAT activity was detected in any of the plant types.

What is claimed is:

1. A plant cell which contains stably integrated into its genome a gene expression cassette, said gene expression cassette comprising a first promoter operatively linked to a sequence comprising an alcR coding sequence from *Aspergillus nidulans* and which encodes an ALCR regulator protein, and an inducible promoter from an ALCR-activatable gene, which gene is the alcA gene from *Aspergillus nidulans*, operatively linked to a target gene, said inducible promoter being activated by the ALCR regulator protein in the presence of an alcohol and/or ketone inducer, so that application of a sufficient amount of a suitable inducer causes expression of the target gene.

2. A plant cell according to claim 1 wherein the inducible promoter comprises part of the CaMV35S promoter.

3. A plant tissue comprising a plant cell as claimed in any one of the preceding claims.

4. A plant comprising a plant tissue as claimed in claim 3.

5. A progeny plant derived from a plant as claimed in claim 4, wherein said progeny plant comprises said gene expression cassette.

6. A seed derived from a plant as claimed in claim 4, wherein said seed comprises said expression cassette.

7. A method for controlling plant gene expression comprising transforming a plant cell with a chemically-inducible gene expression cassette which has a first promoter operatively linked to a sequence comprising an alcR coding sequence from *Aspergillus nidulans*, and which encodes an ALCR regulator protein, and an inducible promoter from an ALCR-activatable gene, which gene is the alcA gene from *Aspergillus nidulans*, operatively linked to a target gene, said inducible promoter being activated by the ALCR regulator protein in the presence of an alcohol and/or ketone inducer, so that application of a sufficient amount of a suitable inducer causes expression of the target gene.

8. A plant cell containing a chimeric promoter operatively linked to a target gene, said chimeric promoter comprising an upstream region containing a promoter from an ALCR-activatable alcA gene from *Aspergillus nidulans* and a downstream region containing a transcription initiation sequence, wherein the upstream region and the downstream region are heterologous and the chimeric promoter is inducible by an alcohol and/or ketone, so that application of a sufficient amount of a suitable inducer, in the presence of the ALCR regulator protein encoded by the alcR gene from *Aspergillus nidulans*, causes expression of the target gene.

9. A plant cell as claimed in claim 8 wherein the chimeric promoter is stably incorporated in the plant cell's genome.

10. A plant tissue comprising a plant cell as claimed in claim 9.

11. A plant comprising a plant tissue as claimed in claim 10.

12. A progeny plant derived from a plant as claimed in claim 11, wherein said progeny plant comprises said chimeric promoter.

13. A seed derived from a plant as claimed in claim 11, wherein said seed comprises said chimeric promoter.

14. A plant cell as claimed in any one of claim 1–2 or 8–9 which is a monocotyledonous plant cell.

15. A plant cell as claimed in claim 14 which is a maize cell.

16. A plant cell as claimed in any one of claim 1–2 or 8–9 which is a dicotyledonous cell.

17. A plant cell as claimed in claim 16 which is a tobacco cell.

* * * * *